US007428705B2

(12) United States Patent
Ronald et al.

(10) Patent No.: US 7,428,705 B2
(45) Date of Patent: Sep. 23, 2008

(54) WEB MAP TOOL

(75) Inventors: Simon Paul Ronald, Adelaide (AU); Stephen Dennis Kirkby, Norwood (AU); Richard John Webber, North Lambton (AU)

(73) Assignee: Maxamine International Pyt Ltd, Adelaide (AU)

( * ) Notice: Subject to any disclaimer, the term of this patent is extended or adjusted under 35 U.S.C. 154(b) by 426 days.

(21) Appl. No.: 10/148,495

(22) PCT Filed: Nov. 30, 2000

(86) PCT No.: PCT/AU00/01480

§ 371 (c)(1), (2), (4) Date: Aug. 23, 2002

(87) PCT Pub. No.: WO01/40988

PCT Pub. Date: Jun. 7, 2001

(65) Prior Publication Data

US 2003/0038836 A1 Feb. 27, 2003

(51) Int. Cl.
*G06F 3/00* (2006.01)
(52) U.S. Cl. .................. 715/738; 715/737; 715/853; 715/854; 715/855
(58) Field of Classification Search .............. 715/738, 715/760, 853, 854, 855, 838
See application file for complete search history.

(56) References Cited

U.S. PATENT DOCUMENTS 5,546,529 A  8/1996  Bowers et al.
5,774,123 A * 6/1998  Matson ................. 715/854
5,845,263 A * 12/1998  Camaisa et al. ............ 705/27
5,870,559 A  2/1999  Leshem et al.
5,877,766 A * 3/1999  Bates et al. ................. 715/854
5,963,914 A * 10/1999  Skinner et al. .............. 705/11
6,035,330 A * 3/2000  Astiz et al. ................. 709/218
6,088,030 A  7/2000  Bertram et al.
6,237,006 B1 * 5/2001  Weinberg et al. ......... 707/103 R
6,369,819 B1 * 4/2002  Pitkow et al. .............. 345/440
6,374,260 B1 * 4/2002  Hoffert et al. ............ 707/104.1
6,470,383 B1 * 10/2002  Leshem et al. ............. 709/223

(Continued)

FOREIGN PATENT DOCUMENTS

EP          0 950 960 A2    10/1999

OTHER PUBLICATIONS

Peter Domel, Webmap—A Graphical Hypertext Navigation Tool, Sep. 1, 1994, pp. 1-14.*

(Continued)

*Primary Examiner*—David A Wiley
*Assistant Examiner*—Boris Pesin
(74) *Attorney, Agent, or Firm*—Edell, Shapiro & Finnan, LLC

(57) ABSTRACT

A method of mapping at least a part of one or more web sites having web objects and web links is provided, whereby web objects and links are mapped as nodes and edges, respectively, in one or more web maps, each object being mapped to at least one corresponding node. The method allows a user to re-display selected items in a web map such that the item are distinguished from other items in the web map and are displayed in a clarified form. This enables a web map to be de-cluttered.

34 Claims, 16 Drawing Sheets

U.S. PATENT DOCUMENTS 6,775,659 B2 *  8/2004  Clifton-Bligh ................. 707/1
2003/0197743 A1 * 10/2003  Hill et al. .................... 345/853

OTHER PUBLICATIONS

"WebCutter: A system for Dynamic and Tailorable Site Mapping" (Maarek et al.) Sixth International WWW Conference, Santa Clara, California, Apr. 1997.

"Visualizing Search Results using SQWID" (McCrickard et al.) Georgia Institute of Technology, Sixth International WWW Conference, Santa Clara, California, Apr. 1997 Poster Session.

"Mapping and Browsing the Web in a 2D Space" (Huang et al.) DEX '99.

"Information Drill-down using Web tools" (Jern) IEEE Conference on Information Visualization IV'97.

* cited by examiner

WEB MAP TOOL

TECHNICAL FIELD

The present invention concerns a method of representing the structure of one or more internet or intranet web sites.

BACKGROUND OF THE INVENTION

The internet is a communications network which connects millions of computers around the world. Many organisations host web sites that can be accessed via this communications network. Each web site can contain a variety of web objects, including plain text, hypertext, images, audio, video, and other multimedia information. In particular, hypertext documents written in Hypertext Markup Language (HTML) and similar languages are referred to as web pages. Many web objects—in particular, web pages—contain links to other web objects, including objects on other web sites. The collection of all web sites and the links between them are known as the World-Wide Web (WWW).

Web sites are accessed using a web browser. To access a web object, a user simply needs to input into a browser the "address" of the object, which is specified by a Uniform Resource Identifier (URI), the most common form of which is a Uniform Resource Locator (URL).

A user of a web site often has needs which are different from the needs of the host of the web site. For example, a user of a corporate web site may be looking for an interactive, interesting and efficient way of accessing information, while the web site host may be interested in raising revenue through sales on the web site, imparting particular product information to the user, or increasing brand recognition with the user. Web site designers therefore face the challenge of meeting the objectives of both the web site host and the users. Web site designers often strive to design a site such that a user can enter the site and quickly retrieve the information that they require, and preferably be provided with other information which is related to the retrieved information. If the web site is poorly designed, or suffers from problems of structural quality and integrity, the user may give up and seek an alternative way of finding the information they require.

Designing and managing a corporate web site can be particularly difficult as such sites are typically large and complex. Information contained in web sites may quickly become out of date, and is frequently added to, changed, or removed. Coordinating these changes can be difficult, as many people can be involved in the process, and many managers and technical staff may not fully understand the structure and organisation of their corporate web site. The web site is usually understood as a complex collection of web pages and links. However, the linking structure of a web site is critical, as it directly affects how well a user can make use of the information provided by the organisation.

A well-designed and well-maintained linking structure that is free from errors has the following benefits:

it helps a user to identify the navigation choices available to them at each web page;
it allows a user to quickly find and read relevant information in the web site; and
it allows the organisation to lead a user to information that they would like the user to see, such as an order page or a corporate mission statement.

Unfortunately, large web sites often have a poorly-designed and poorly-maintained linking structure, and may exhibit any of the following common problems:

broken links (links to objects which no longer exist or have changed URL);
isolated (unreachable) objects;
objects which are out-of-date;
non-returning links (links which lead the user into a dead end);
objects which are hard to reach (a large number of links must be traversed);
important web objects (such as order forms) which are only linked from a few web pages; and
inconsistent linking styles and techniques.

These problems reduce the effectiveness of the web site and leave the user with a poor impression of the organisation hosting the web site.

An intranet is a web site hosted by an organisation for internal use only, such as for employees. Many organisations have intranet web sites that are much larger than their public web site, as the internal need for information within the organisation may be more urgent than the need to provide information to the public. As a result, the inconsistencies that occur in a typical internet web site are of even more concern within intranet web sites.

Web maps have been developed as a tool to help a user understand the structure of a web site. A web map can represent how a user might navigate between pages in the web site. In this context, web maps are also referred to as navigation maps or access paths.

A web map is a representation of one or more web sites, or parts thereof. A web map can be created by scanning one or more web sites, examining the web objects encountered, and recording the linking structure associated with these objects. Each web object may be represented in a web map by a node, which can be an icon, symbol, shape or text. Often, the node is labelled with the filename, title, or URL of the associated web object. One or more links between a pair of web objects can be represented in a web map by an "edge", which is drawn as a line between the associated nodes. Typically, an arrowhead is placed on the line to indicate the "direction" of the link from the object containing the link (called the source of the link) to the object referenced by the link (a URL, called the destination of the link). If there are links running in both directions between a pair of web objects, the corresponding edge may have arrowheads on both ends.

Definitions

A web site includes a collection of web objects which may provide information via an internal network (an intranet web site) or to the general public via the internet (an internet web site). A web site may also have facilities for obtaining information from its users. Note that a web site may consist of more than one physical machine. For example, a corporation called Acme may have two machines whose internet addresses are, respectively, www.customers.acme.com and www.products.acme.com, and there may be many links that relate web objects across the two machines. The organisation may consider both machines to constitute a single logical web site.

A web object is any document that can exist on a web site. This includes, but is not limited to, plain text, hypertext, images, audio, video and other multimedia objects, executable applications, and database information. A web object may be a static file or database entry residing on a machine hosting the web site, or it may be dynamically generated by the web site as needed.

A directory structure of a web site is the physical arrangement of web objects on the machine or machines hosting the web site. The term directory structure is used herein not only in the context of web objects stored in traditional file systems, but also for web objects stored in relational databases, object-oriented databases, and any other structured storage of web objects.

A linking structure of a web site is the arrangement of web objects and links which form a web site.

A web map is a representation of the linking structure of one or more web sites or parts thereof.

A "directory distance" between two web objects is given by the length of the shortest path between the two objects in the directory structure of the web site. For example, "www.abc.com" and "ftp.abc.com" would be in the same virtual directory, namely ".abc.com", and ".com" is a common grandparent directory.

A "link distance" between two web objects is the length of the shortest path between the two objects in the linking structure of the web site.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

SUMMARY OF THE INVENTION

A first aspect of the present invention provides a method of mapping at least a part of one or more web sites having web objects and web links, whereby web objects and links are mapped as nodes and edges, respectively, in one or more web maps, each object being mapped to at least one corresponding node, and there being only one corresponding object for each node, the method comprising the steps of:
  (a) selecting one or more sets of items for display in the respective one or more web maps, wherein items include nodes and edges corresponding to web objects and links in the least one web map;
  (b) displaying the one or more sets of items in the respective one or more web maps;
  (c) selecting at least one item from the displayed sets of items; and
  (d) re-displaying the at least one item in at least one web map such that the item is distinguished from any other items in the web map.

The method according to the first aspect of the invention may be performed on or with the aid of a computer.

Steps (a) and (b) of the method may be either automatic, or guided in response to instructions from a user, and may comprise selecting and displaying either all of the nodes and links in the at least one section of the web map, or a subset of those nodes and links. Preferably, the steps (b) and (d) of the method comprise displaying items in a graphical format. In some cases, web maps may partially or substantially overlap such that one or more items is common to a plurality of web maps. An object may therefore be mapped as more than one corresponding node. However, for each node there is only one corresponding object.

Steps (c) and (d) have the advantage that they can be used to display a web map in a clarified format, making the information in the web map easier to digest. For example, the method provides the option of omitting nodes and/or edges which are not of interest in a web map, thereby "de-cluttering" a web map. A user is thus able to focus on the remaining parts of a web map without distraction. Such methods have numerous applications, as even well-designed web sites may result in web maps which each contain hundreds of nodes and thousands of edges.

Items may be selected in step (c) directly, such as by designating items and selecting the designated items. Alternatively, items may be selected indirectly by designating items, and selecting all items which are not designated. Step (c) offers the option of displaying a subset of items in a web map. Step (c) may comprise searching through items in the one or more web maps and filtering out items which are not to be selected. Step (d) may comprise one or more of the following sub-steps:
  emphasising or highlighting selected items; or
  deleting any item which is not selected in step (c).

Alternatively, step (c) may not necessarily involve selecting a subset of items in a web map. In one embodiment, step (c) comprises selecting all items in one or more web maps. In this embodiment, all of the items are re-displayed in step (d). Step (d) may comprise a sub-step of rearranging the selected items. For example, the selected items may be sorted or categorised accordingly to instructions from a user.

Step (c) may be carried out in one or more of the following ways:
  manually, such as by designating particular features with a cursor; or
  semi-automatically, such as by operating a searching tool or filter in response to instructions from a user; or
  automatically;

Semi-automatic selections may comprise a user operating a searching tool to select items in a web map. For example, a user may choose to select a subset of nodes which correspond to objects of a particular size and type. Selected items may optionally be further subjected to a manual selection sub-step in which a user manually selects a smaller subset of features, such as by using a cursor to designate particular nodes and edges to be displayed. Manual and/or semi-automatic selections may be preceded by an automatic selection. For example, an automatic selection may comprise selecting all objects and links of a particular web site, or only particular types of objects and links.

The one or more sets of items may be selected in step (a) according to the following sub-steps:
  (a1) for each of the objects in the part(s) of the web site(s) to be mapped, adding a node to the sets of items such that similar nodes are added to the same set, wherein the similarity of any pair of nodes is a function of one or more of the following:
    a directory distance, being a measure of separation between a pair of web objects corresponding to the pair of nodes in a directory structure of the one or more web sites;
    a link distance, being a measure of separation between a pair of web objects corresponding to the pair of nodes in a linking structure of the one or more web sites;
  (a2) for each first object which corresponds to a node added to a set, adding a new node to the set for any object which is either the source of a link to the first object, or a destination of a link from the first object;
  (a3) for each pair of nodes in each web map, adding an edge between the pair of nodes if there is a link between a pair of objects corresponding to the nodes.

Preferably, the contributions of the link distance and the directory distance to the similarity criterion of pairs of nodes can be adjusted, depending on the type of web map required. Preferably, the adjustment can be made by a user.

Sub-steps (a1)-(a3) offer the possibility of creating web maps which simultaneously represent both the directory structure and the linking structure of one or more web sites. In one embodiment, the similarity of a pair of nodes is controlled by a parameter $\alpha$, wherein:
  only the directory distance $\alpha$ contributes if $\alpha=0$;
  only the link distance contributes if $\alpha=1$; and as α increases, the contribution of the link distance increases and the contribution of the directory distance decreases.

An example of an equation in which the link distance L and directory distance D are combined to give the overall distance x(a, b) between web objects a and b is:

$$x(a, b) = (1-\alpha)D + \alpha L \quad (1)$$

The resulting distance x(a, b) can then be used as a "dissimilarity measure" in a geometric clustering algorithm, such as the PAM (Partition Around Medoids) algorithm or the CLARANS (Clustering Large Applications based on RANdomised Search) algorithm. Alternatively, the distance x(a, b) can be used as a weighting factor for the edges in a map which combines directory structures and linking structures of a web site. Such a graph can be partitioned using a weighted graph partitioning algorithm, such as the Ratio Cut algorithm. The resulting clusters of nodes are then assigned to separate web maps.

Step (c) may comprise sub-steps of searching through some or all types of items in a web map and determining, based on predetermined selection criteria, whether each item should be selected. Known searching tools may be used to implement these sub-steps. The selection criteria may be set by a user, and may be based on specifying a set of properties that the selected items should possess, or alternatively, should not possess. Properties which may be used in the selection criteria include one or more of the following:

- the type of web object (for example, general types such as plain text, hypertext, images, audio, video, other multimedia objects, executable applications, missing entity or specific file formats);
- the form of a web object (for example, title, file name, attributes, metadata);
- the connectivity of a web object (for example, the number of links into or out of a node);
- traffic-derived properties of a web object (for example, the number of hits to an object over a predetermined period of time);
- a set of keywords, ideas, topics, or data patterns to be found within a web object;
- a set of constraints on the properties and attributes of a web object;
- the size of the web object, either as a number (for example, the number of bytes, printable characters, words, or lines), or as a category (for example, "small", "medium" or "large");
- whether the web object is a web page in its own right, or some other web object (such as an embedded image) which is included in a web page;
- whether the web object is part of the web sites being represented by the web map, or a web object on another web site;
- whether the web object is a web page containing frames;
- whether the web object is a web page containing forms;
- other properties as determined by some characteristic of the web object or of the web object's contents; or
- a power search (for example, using a boolean expression combining any of the above selection criteria).

A graphical representation of a node may consist of an icon, symbol, shape, text, or any combination of these. Graphical properties of a node include the number, types, sizes, colours, intensities, textures and relative positions and orientations of its components and its overall size.

The directions of links to or from a designated set of nodes may be used as a selection criterion. For example, nodes may be selected if they are the source of one or more edges having destinations in a subset of nodes designated by a user. Further, nodes may be selected if they are the destination of one or more edges having sources which are among a designated subset of nodes. Further, nodes may be selected if they are either the source or destination of one or more edges having destinations or sources, respectively, among a designated subset of nodes. Preferably, if a node is not selected, all edges for which that node is either a source or destination are also not selected.

Items may also be selected in step (c) as a result of executing a third party program, function or routine which communicates with a web mapping system through an application programming interface (API). The third party program may be:

- a custom-developed program developed by a third party in a software language such as C or Java; or
- a custom-developed program that interacts with one or more third party software systems such as relational database systems, spreadsheets, object-oriented database systems and knowledge search systems.

In determining which nodes are to be selected, the third party program may have access to the following information in a web map through the API:

- how nodes are interconnected by links in the web map;
- properties of the nodes, such as the document title, the size of the web page, the modification date; or
- properties of edges in the web map, such as link text, what type of link the edge represents (such as a secure https link, an embedded image link, or a hyperlink as a result of an <A> HTML tag).

Similarly, items selected in step (a) or step (c) may be displayed as a result of executing of a third party program, function or routine which communicates with a web mapping system through an application programming interface. The third party program may display selected items using web maps, graphs, charts, tables, reports, or other known diagram types, or may provide page and link information in conjunction with corresponding web maps. The third party program may have access through the application programming interface to various properties and attributes of the web maps, including properties and attributes of nodes and edges.

Step (d) may involve creating an overview web map. Creating an overview web map may comprise the following sub-steps:

- assigning a map-node to the overview web map for each web map;
- adding an edge between each pair of map-nodes which represents web maps of web objects joined by one or more links.

The overview web map provides the advantage that it can be used to jump to an arbitrary web map, and provides a high-level description of the web sites represented by the set of web maps. Preferably, the overview web map is such that if a user selects any one of the map-nodes, the web map corresponding to that web node is displayed. An overview web map may be displayed alongside one or more normal web maps.

The method of the present invention may be used to map a directory or sub-directory containing a large number of "pages", that is, web objects which do not link beyond the directory. For example, a directory may include 1000 or more pages and a web map of such a directory would be far too cluttered to identify node attributes if all pages were displayed. Step (c) may be used to select and display more manageable subsets of nodes representing pages, such as 15 nodes at a time. In one embodiment of step (c), provision is made for a user to arbitrarily select and display subsets of nodes.

For example, steps (a) and (b) may display all of the pages in a condensed format, such as with "overview nodes" which each represent a subset of nodes, such as 10 nodes. This enables a muser to select and display any one of the subsets of nodes by designating an appropriate overview node. The condensed format has the advantage of allowing a user to move from one subset of pages to another, thereby providing "loosely-coupled" web maps. Step (d) may involve displaying a selected web object or objects in a viewing tool, such as a web browser.

A further embodiment of step (c) comprises selecting web map items which have changed over a given time interval. A web map item may be selected if one or more of the following circumstances exists:
- the corresponding web object or link has been altered;
- the corresponding web object or link has been deleted from a web site;
- the corresponding web object or link has been added to a web site;
- the corresponding web object or link has been moved within a web site;

In this embodiment, step (c) comprises a sub-step of scanning each web site at two distinct times A and B. Step (d) may comprise creating one or more web maps representing the web site(s) at either time A or time B, such that the properties of preselected nodes or edges corresponding to, respectively, web objects and links, are modified to highlight:
1. web objects or links which existed in the web sites at time A but did not exist at time B;
2. web objects or links which existed in the web sites at time B but did not exist at time A;
3. web objects which have been altered between times A and B; or
4. web objects which have been moved between times A and B.

Step (d) may be subjected to the following additional constraints:
- each node corresponding to a web object which existed at both times A and B is displayed at approximately the same position in the web maps corresponding to time B as in the web maps corresponding to time A; and
- each node corresponding to a web object which existed at time B but did not exist at time A is displayed at a position "close" to those nodes to which it is connected by an edge.

This embodiment may be initiated upon the occurrence of one or more of the following:
- a button click, a menu operation, a command, or some other user operation;
- at periodic time-intervals that are fixed, variable, or determined by a predefined schedule;
- when a change is made to the web sites, a change being defined as the addition, movement, removal or modification of one or more web objects, or the addition, movement, removal or modification of one or more links.

The method of the present invention may further comprise the following step:
(e) providing information about web objects and/or links which correspond to preselected items in the one or more web maps.

Step (e) may comprise gathering and displaying additional information related to operation or performance of a web map or corresponding web sites. Step (e) may also comprise generating a report which may be displayed to a user automatically or on demand. The preselected items may be the items selected in step (c). Alternatively, step (e) may comprise a sub-step of preselecting items from the one or more web maps. Information is only provided in respect of the preselected items.

Step (e) may occur in response to a query from a user. The information may be obtained by interrogating relevant parts of the corresponding web site(s). The query may be a request for specific information, such as data about items selected in step (c). For example, a user may request to know how many and which of the selected nodes correspond to objects with a size in a particular range. In one embodiment, step (c) comprises selecting a subset of web map items and step (e) comprises performing a search limited to the selected items.

Alternatively, the query may be a two-part query, a first part of the query being a preselection, and the second part of the query being a request for information about items found (ie. preselected). As with step (c), the preselection sub-step in step (e) may be made manually, semi-automatically, automatically, or combinations of these. The preselection sub-step may involve searching through some or all types of items in a web map, and deciding, based on predetermined selection criteria, whether each item should be preselected. Known searching tools may be used for this purpose. The preselection criteria may be set by a user, and may be based on specifying a set of properties that the selected items should possess, or alternatively, should not possess. The same properties which may be used as selection criteria in step (c) may also be used as preselection criteria in step (e).

Results provided in response to a search query may be presented in a graphical format. For example, preselected nodes or edges may be highlighted in some way, such as by using a different colour, size, shape or pattern. Information about the preselected items may be presented using graphs, charts, diagrams, or other known techniques. A statistical analysis of the data may also be provided using known techniques. The results of a search query may include a calculated relevancy value for each item found. The calculation of each relevancy value may be based on a comparison of the properties of each web object with the search criteria used. The relevancy value of each searched item may be presented in a number of ways, including tabulated data, graphs or charts in respect of the searched nodes, or by graphically altering a representation of each searched node (colour, size, shape or pattern). The web pages corresponding to preselected nodes may be displayed, possibly highlighting parts of the documents which "matched" the search criteria.

An embodiment of step (e) comprises the sub-step of calculating the amount of information in each web object which corresponds to a pre-selected node. The amount of information in each web object may be determined by combinations of one or more of the following:
- the time it is expected to take to transfer the web object from the web site to a web browser;
- the size of the web object plus the size of all web objects embedded in that object, where size is as above;
- the time it is expected to take to transfer the web object and all web objects embedded in that object from the web site to the web browser;
- the number of links from the web object to other web objects on the same web site;
- the number of links from the web object to other web objects on another web site; or
- some other measure of the size of the web object.

This information is useful for identifying overly large web pages, which are a sign of a poorly-designed web site, and may cause difficulty when a user attempts to access them. For example, the size of each web object may be represented by the size of the icon of its corresponding node.

Calculations on the amount of information in each web object may be used to determine:
- the properties of each node;
- the absolute position of each node in its web map; or
- the relative positions of the nodes in each web map.

In a further embodiment, step (e) comprises counting, for each pair of objects corresponding to preselected nodes in the web maps, the number of links for which one of the objects is a source and the other of the objects is a destination. For example, the number of links between two web objects may be represented by the number of arrowheads on the corresponding edge. The counted number of links may be used to determine properties of the edge between the pair of nodes corresponding to the pair of web objects.

In a further embodiment, step (e) comprises providing information, either in a web map or in a report, about links existing between two preselected web objects corresponding to two designated nodes. For example, a user may preselect two nodes by designating an edge between the two nodes in a web map. The provided information may comprise:
- the text of each link in a web page which is the source of the link;
- the position (for example, the section name or line number) of each link within each containing web page;
- the type of each link (hyperlink, embedded object, frame relationship, form relationship, or image-map relationship);
- or any other information specific to each link.

In a further embodiment, step (e) comprises displaying web pages containing links which correspond to a preselected edge in a web map. Optionally, highlighting may be provided in sections of the web pages which contain one of the links. For example, the appropriate web pages may be displayed as a result of a user preselecting an edge in a web map.

A further embodiment of step (e) comprises providing information about links corresponding to edges whose common destination is a preselected node in a web map, and about web objects which are the sources of these links. The information may be displayed in a web map or a report, and may include:
- the title and/or URL of each source web object;
- the text of each link in its source web object;
- the position (for example, the section name or line number) of each link within its source web page;
- the position (for example, the section name or line number) of the destination of each link within its destination web object;
- the type of each link (hyperlink, embedded object, frame relationship, form relationship, or image-map relationship);
- any other information specific to each link.

A further embodiment of step (e) comprises determining the number of hits to one or more web objects corresponding to preselected nodes over a predetermined time interval and presenting this information to a user. For example, a user may specify a time interval, and a server log file or some other web-server-based repository of information may be examined to determine the number of hits over the time interval. Step (e) may further comprise updating the properties of each node to represent the number of hits to the corresponding web objects. Information about the number of hits is useful for web designers, as it lets them identify the "popular" web objects from which they can guide users to order forms and other priority web objects. It also clearly shows those web objects which are rarely accessed, and may need to be repositioned or discarded. For example, the number of hits to a particular web object may be represented by a "halo" around the icon of the web object—the darker the halo, the more hits were recorded to that web object within the given time interval.

A further embodiment of step (e) comprises determining an approximate aggregate usage of links corresponding to preselected edges over a predetermined time interval and presenting this information to a user. Where an edge corresponds only to links in a single direction, the properties of the edge may be updated to represent an aggregate of the corresponding links. Where an edge corresponds to links in both directions, the edge may be graphically divided into two segments, such that:
- the properties of the segment closest to a node represents aggregate usage information of the links whose destination is the corresponding web object; and/or
- the proportion of the lengths of the segments is equal to the proportion of the aggregate usage information in each direction.

For example, a user may specify a time interval, and a server log file or some other web-server-based repository of information may be examined to determine the approximate aggregate usage of links.

A further embodiment of step (e) comprises determining the number of form submissions to at least a part of a web site (corresponding to preselected items in a web map) over a predetermined time interval and presenting this information to a user. Submissions may be aggregated according to:
1. a web page containing the form; or
2. a program on the web site which process the form; or
3. a combination of 1 and 2; and If submissions are aggregated according to 1, the properties of the node corresponding to the web page containing the form may be updated. If submissions are aggregated according to 2, the properties of the node corresponding to the program which processes the form may be updated. If submissions are aggregated according to both 1 and 2, the properties of the edge corresponding to the link between the web page containing the form and the program which processes the form may be updated.

A further embodiment of step (e) comprises presenting information about web objects corresponding to preselected nodes. The information may be presented in the web maps or a report, and may include:
- which keywords were found in each web page;
- the number of keywords found in each web page;
- what other related keywords, topics or ideas were located in each web page;
- how a relevancy value is calculated for each web page; or
- which keywords occurred in the context of links in each web page, and which keywords appeared in the context of non-link text in each web page.

A further embodiment of step (e) comprises presenting information about the directory position of each web object within the directory structure of the web sites. The information may be denoted in each web map by:
- text located on or near each node corresponding to the web object; or
- modifying the properties of each node such that nodes corresponding to web objects in the same directory share common properties; or
- positioning the nodes in each web map such that all nodes corresponding to web objects in the same directory are grouped into a common region of the web map.

The method according to the present invention may further comprise the following step:

(f) modifying the one or more web sites in response to a modification of a corresponding web map by a user.

One embodiment of step (f) comprises the sub-step of presenting a selected web object in a hypertext editor, or some other editing tool appropriate to the type of web object, in response to a selection of the corresponding node by a user. The user is preferably permitted to edit the object when it is presented, and thereby change the web site. The web maps may be updated to maintain their consistency with respect to the changes made to the web site.

In another embodiment of step (f), web objects may be moved by a user from one directory to another by any combination of the following:

selecting the nodes corresponding to the web objects, then selecting the new directory; or "dragging" the nodes corresponding to the web objects onto a web map, region, or node corresponding to the new directory; or some other manipulation of the web maps.

Each link in the web sites whose destination is one of the moved web objects may be updated to reflect the new directory containing the web object. The web maps may be updated to maintain the consistency of the directory position information presented therein. This embodiment may be used to insert a new web object into a web sites at a particular directory position by selecting the corresponding node, edge or web map. For example, the user may be required to specify the type of web object to be created and then invoke a hypertext editor, or some other editing tool appropriate to the type of the new web object, to create the contents of the object. Preferably, the web maps are then updated to include the new web object.

A further embodiment of step (f) comprises deleting a user-selected subset of one or more nodes from web maps, and deleting all web objects which correspond to the deleted nodes. Preferably, any link whose source or destination is one of the deleted web objects is also deleted from the web sites. For each such link, if its source web object is not among the deleted web objects, then the user is preferably able to invoke a hypertext editor, or some other editing tool appropriate to the type of source web object, to remove the context of the link. The web maps are preferably also updated to maintain their consistency with respect to deleted web objects and the new linking structure.

In a further embodiment of step (f), the destination of one or more links can be changed by combinations of one or more of the following:

selecting edges corresponding to the links, and then selecting the node corresponding to the new destination web object; or "dragging" the arrowhead of the edge corresponding to a link onto the node corresponding to the new destination web object; or some other manipulation of the web maps.

A hypertext editor, or some other editing tool appropriate to the type of web object containing a link, can be invoked by the user to change the context of the link to be consistent with its new destination web object. Preferably, the web maps are updated to maintain their consistency with respect to the new linking structure.

In a further embodiment of step (f), a new link can be added to web sites by combinations of one or more of the following:

1. selecting a node corresponding to the source web object of the new link, and then selecting the node corresponding to the destination web object of the new link; or 2. "dragging" the node corresponding to the source web object of the new link onto the node corresponding to the destination web object of the new link; or 3. some other manipulation of the web maps.

A hypertext editor, or some other editing tool appropriate to the type of web object containing a link, can be invoked by the user to create the context of the link to be consistent with its new destination web object. A web browser, hypertext editor, or some other viewing or editing tool appropriate to the type of web object which is the destination of the link, can be invoked by the user to specify the section of the destination web object to link Preferably, the web maps are updated to maintain their consistency with respect to the new linking structure.

In a further embodiment of step (f), one or more edges can be selected from the web maps corresponding to links which are then deleted from the web sites. If there are multiple links corresponding to a selected edge, the user can select from among these links by:

using one or more keys on a keyboard; or selecting one or more menu items on the web maps or the windows containing the web maps; or cycling through the possible links, such as by clicking with a mouse or some other selection device; or some other means of selecting from a list of possible links.

Step (f) may invoke a hypertext editor, or some other editing tool appropriate to the type of web object containing the link, to remove the context of the link. Preferably, the web maps are updated to maintain their consistency with respect to the new linking structure.

The method according to the present invention may further comprise the following step:

(g) re-displaying at least one web map after the web map has been modified in step (f).

In one embodiment of step (g), a web map is re-scaled to best occupy space provided for its display after the web map has been modified by any of the above methods. The re-scaling may occur even where modifications have only been made in decorations of nodes and edges.

Step (b) and /or step (d) may involve displaying a web map in three-dimensions. For example, each node may be drawn as one or more three-dimensional shapes, objects, surfaces or text (for example, spheres cubes and cones) or any combination of these. The graphical properties of each node may include the number, types, sizes, colours, intensities, textures and relative positions and orientations of its components, and its overall size and orientation. Each edge may be drawn as a pipe, tube, line or some other elongated shape, or a continuous sequence of such shapes, which may be decorated with three-dimensional shapes, objects, surfaces or text—in particular, three-dimensional arrowheads—or any combination of these. The graphical properties of each edge may include the cross-sections, thicknesses, continuities, colours, intensities and textures of its shapes, and the number, types, sizes, colours, intensities, textures and relative positions and orientations of its decorations. All of the above methods which are applicable to web maps are also applicable to three-dimensional web maps by simple modifications of the appropriate graphical properties.

A second aspect of the invention provides a method of providing information to a third party computer program about at least a part of one or more web sites having web objects and web links, the method comprising the steps of:

mapping the web objects and links as virtual nodes and virtual edges, respectively, in one or more virtual web maps, each object being mapped to at least one corresponding virtual node, and there being only one corresponding object for each virtual node;

selecting one or more sets of items from the one or more virtual web maps, wherein items include virtual nodes and virtual edges corresponding to the web objects and links in the least one web map;

providing information about the selected one or more sets of items to an application programming interface suitable for transmitting at least some of the information to a third party program.

Virtual nodes, virtual links and virtual web maps may be any means of representing the information contained in the corresponding web site(s) without visually displaying the information. For example, each virtual node and link and any attributes may be represented in a data structure stored on a computer readable medium. Virtual nodes and virtual edges in the first aspect of the invention.

A third aspect of the invention provides a method of re-displaying a web map in which web objects and web links of at least a part of one or more sites are mapped as nodes and edges, respectively, wherein the method comprises the steps of:

selecting at least one item from the web map, wherein items include nodes and edges in the web map; and re-displaying the at least one item the web map such that the at least one item is distinguished from any other item in the web map.

The steps of selecting and re-displaying may be implemented in accordance with any of the embodiments of steps (c) and (d), respectively, of the first aspect of the invention.

A fourth aspect of the invention provides a method of re-displaying a web map in which web objects and web links of at least a part of one or more sites are mapped as nodes and edges, respectively, wherein the method comprises the steps of:

selecting one or more sets of items from the web map, wherein items include nodes and edges in the web map; and re-displaying the one or more sets of items in one or more respective new web maps.

The method of the fourth aspect of the invention may further comprise a step of selecting at least one item from the re-displayed set(s) of items. This step may be implemented in accordance with any of the embodiments of step (c) of the first aspect of the invention.

The method of the fourth aspect of the invention may further comprise a step of re-displaying the at least one item in at least one of the new web maps such that the item is distinguished from any other item in the at least one new web map. This step may be implemented in accordance with any of the embodiments of step (d) of the first aspect of the invention.

A fifth aspect of the invention provides a method of re-displaying a web map in which web objects and web links of at least a part of one or more web sites are mapped as nodes and edges, respectively, wherein the method comprises re-displaying the web map in a three-dimensional graphical format.

A sixth aspect of the present invention provides a computer readable medium storing instructions for controlling a computing device to map at least a part of one or more web sites in accordance with the method of the first aspect of the present invention.

A seventh aspect of the present invention provides a computer readable medium storing instructions for controlling a computing device to provide information to a third party computer program in accordance with the method of the second aspect of the invention.

An eighth aspect of the present invention provides computer readable medium storing instructions for controlling a computing device to display a web map in accordance with either the method of the third, fourth, or fifth aspect of the invention.

A ninth aspect of the present invention provides a system for mapping at least a part of one or more web sites having web objects and web links, whereby web objects and links are mapped as nodes and edges, respectively, in one or more web maps, each object being mapped to at least one corresponding node, and there being only one corresponding object for each node, the system comprising:

means for selecting one or more sets of items for display in the respective one or more web maps, wherein items include nodes and edges corresponding to web objects and links in the least one web map;

means for displaying the one or more sets of items in the respective one or more web maps;

means for selecting at least one item from the displayed sets of items; and means for re-displaying the at least one item in at least one web map such that the item is distinguished from any other items in the web map.

The system includes means suitable for implementing each embodiment of the first aspect of the invention.

A tenth aspect of the present invention provides a system for providing information to a third party program in accordance with the method of the second aspect of the invention.

An eleventh aspect of the present invention provides a system for re-displaying a web map in accordance with either the method of the third, fourth, or fifth aspect of the invention.

In order that the present invention may be more clearly understood, embodiments of the invention will now be described with reference to the accompanying drawings.

DETAILED DESCRIPTION OF THE DRAWINGS

The present invention may be used to prepare a map of: a web site; a part of a web site; multiple parts of a web site; or parts of one or more web sites. Web objects and links are shown as nodes and edges, respectively in a web map. In the present context, the expression "items" is used to mean all types of features displayed in a web map, including nodes and edges.

Information in a web map may be totally or partially generated in a web mapping system by interrogating a web site to obtain data describing web objects and links, and attributes of the web objects and links. Alternatively web site information may be provided by a third party computer program which is responsible for collecting page and link information relating to one or more web sites, and then either sending the information to web maps generated according to the present invention, or allowing the web maps to have on-demand access to the information through an application programming interface. Examples of a third party program include:

spreadsheet software;

graphics software;

a spider-based site crawler that uses the HTTP protocol to gather web site information, including page and link information;

a FTP site crawler that uses the FTP protocol to gather web site information; or a disk scanner that connects to a web site directly using direct disk access either locally or through a network.

Figure 1:
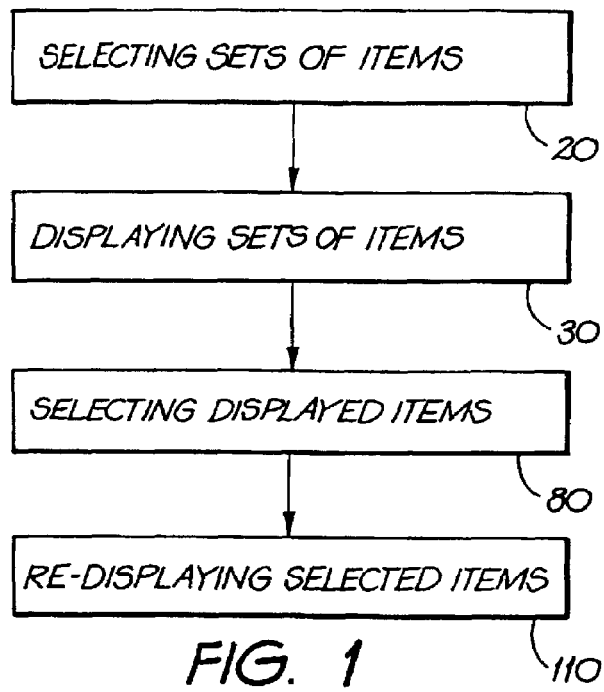
FIG. 1 is a flow chart of an embodiment of the present invention.
Figures 2, 3:
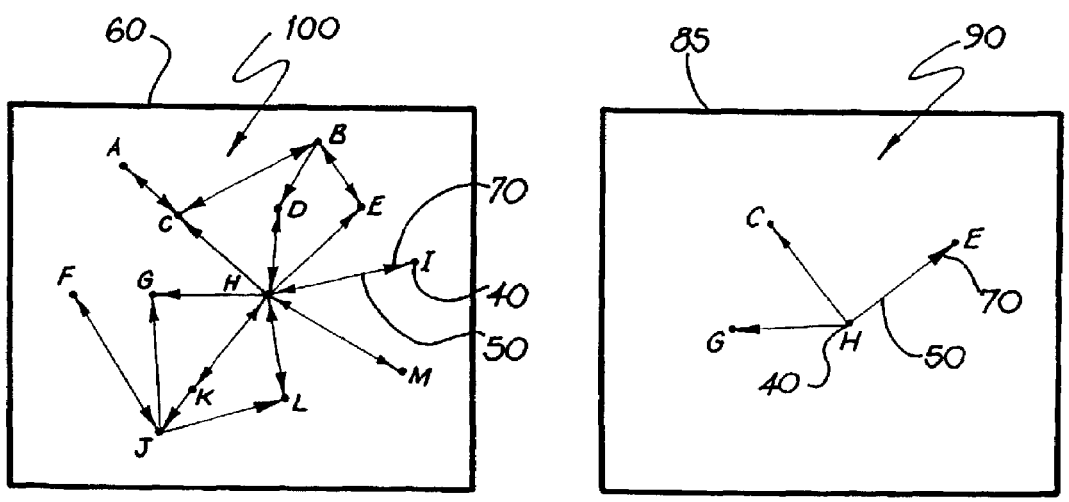
FIG. 2 shows an embodiment of a web map in which a set of items is displayed.
FIG. 3 shows an embodiment of a web map in which a subset of the items in FIG. 2 is displayed.
Figure 4:
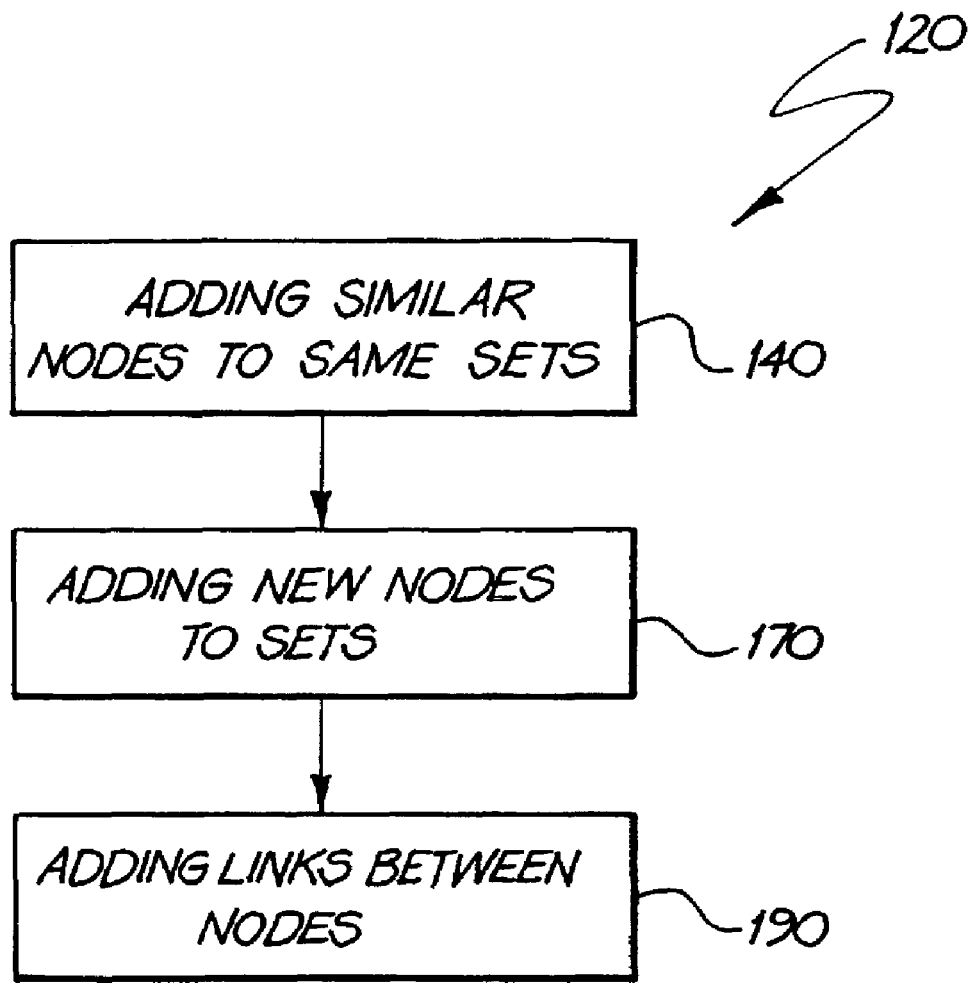
FIG. 4 is a flow chart of sub-steps in an embodiment of a first step of the method shown in FIG. 1.

A first embodiment of a method according to the present invention will now be described with reference to FIGS. 1-3. The first step 20 of the method involves selecting sets of nodes and edges to be displayed in respective web maps. In the embodiment shown, all nodes and edges are to be displayed in a single web map, and are therefore added to a single set. The second step 30 involves re-displaying all of the nodes 40 and edges 50 in a web map 60. In this case, there is only one set, so only one web map 60 is generated. Each edge 50 includes either one or two arrowheads 70 to indicate the directions of links in the corresponding web site. The third step 80 involves creating a new web map 85 by selecting items 90 from the items 100 initially displayed in the web map 60. This step allows a user to simplify the web map 60 by highlighting items of interest 90 and deleting items which are not of interest. In the example shown in FIG. 3, a user has only selected node H, plus those nodes which are the destination of a link from node H, but not the source of a link to node H. Only three nodes satisfy this selection criteria, namely nodes C, G, E and H. Nodes D, I, M, L, K are the destination of a link from node H, but are also the source of a link to node H, and are therefore not selected. In the fourth step 110, only the selected items are re-displayed in the new web map 85.

Figure 5:
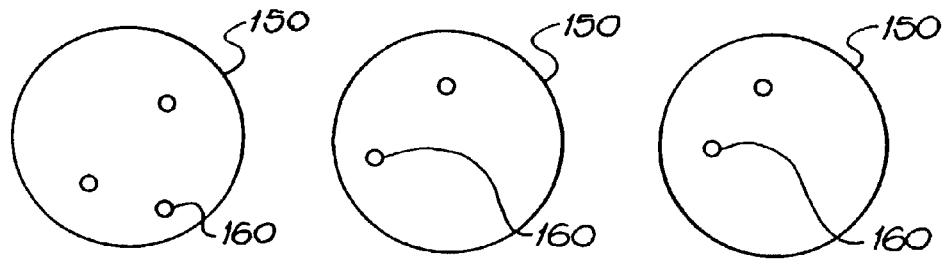
FIG. 5 shows three sets in which nodes have been selected.
Figure 6:
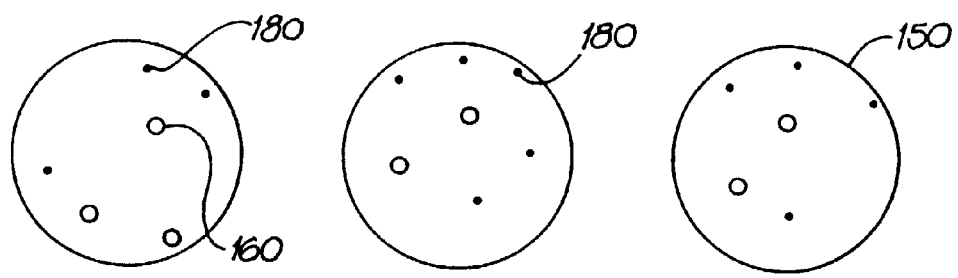
FIG. 6 shows the sets of FIG. 5 with new nodes added to the sets.

A second embodiment of the invention will now be described with reference to FIGS. 1 and 4-7. The first step 20 comprises three sub-steps 120. The first sub-step 140 involves adding "similar" nodes to the same set. FIG. 5 shows three sets 150 of similar nodes 160 which correspond to different sections of a web site. The distance between each pair of nodes 160 is measured as a function of both the directory distance and the link distance between corresponding objects in the web site. Nodes are "similar" when they correspond to objects which are close to each other relative to other objects when proximity is measured as a combination of the directory distance and link distance.

Figure 7:
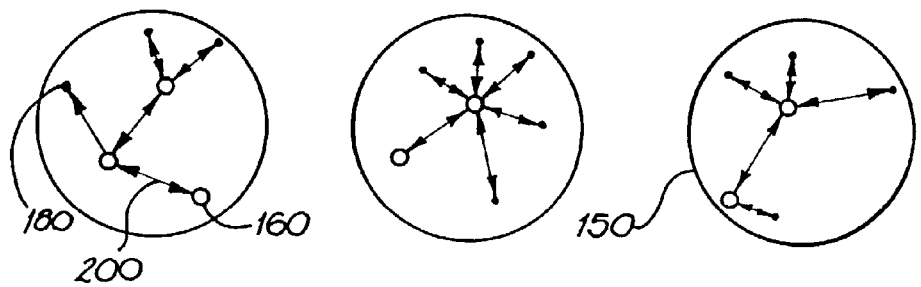
FIG. 7 shows sets of FIG. 6 with edges added to the sets.

The second sub-step 170 (FIGS. 4 and 6) comprises adding new nodes 180 to the sets 150 for each object which is either the destination of a link whose source corresponds to one of the earlier nodes 160, or the source of a link whose destination corresponds to one of the earlier nodes 160. The third sub-step 190 (FIGS. 4 and 7) comprises adding edges 200 to the sets 150 between any pair of nodes 160, 180 for which there is a link between corresponding objects in the web site(s). The three sets 150 of nodes 160, 180 and edges 200 shown in FIG. 7 are the items which are subsequently displayed in three web maps in the second step 30 of the method. Particular items in the web maps can then be selected and re-displayed (third and fourth steps 80, 110 of the method shown in FIG. 1) as with the first embodiment.

Figure 8:
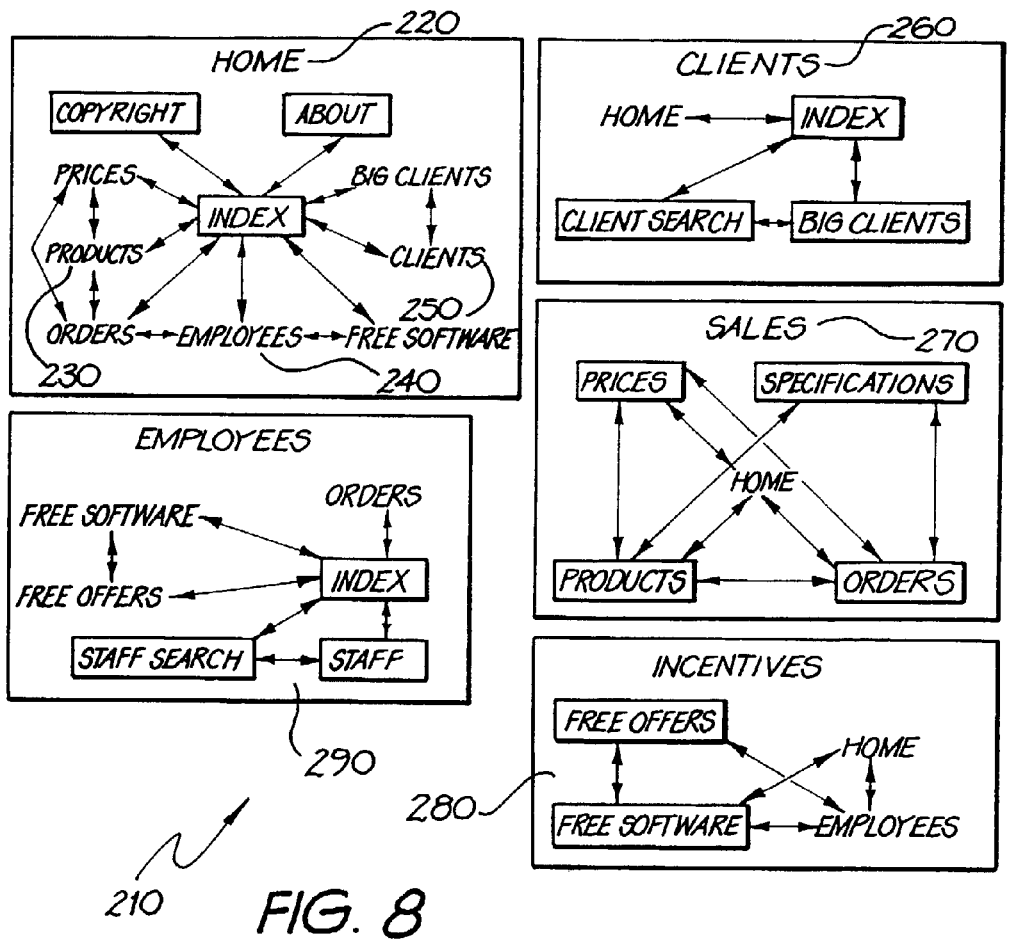
FIG. 8 shows a group of web maps for a web site.
Figure 9:
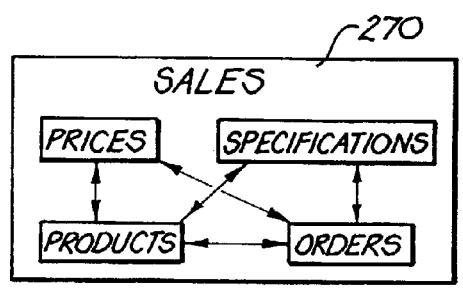
FIG. 9 shows the Sales web map of FIG. 8 after the Home node has been removed.

Another application of sub-steps 120 will now be described with reference to FIG. 8. A set of web maps 210 is shown representing a web site. The web site consists of four directories: a Home directory 220; a Products directory 230; an Employees directory 240; and a Clients directory 250. However, the Products directory 230 contains two separate clusters in the linking structure: a Sales cluster (Products, Specifications, Prices and Orders), and an Incentives cluster (Free Software and Free Offers). In using web mapping techniques of the prior art, this structure would not be revealed. Directory-only partitioning methods would group Sales and Incentives in a single map. Linking-only partitioning would group Employees and Incentives into a single group because there is a direct link between Employees and Free Software. Simultaneously partitioning by directory structure and link structure in accordance with the method shown in FIG. 4 produces four web maps, namely Clients 260, Sales 270, Incentives 280 and Employees 290, and effectively reveals the structure of the web site. FIG. 9 illustrates the Sales web map 270 after the third and fourth steps 80, 110 of the method shown in FIG. 1 have been applied. In this example, all nodes have been selected except the Home node 220 in the Sales web map 270.

Figure 10:
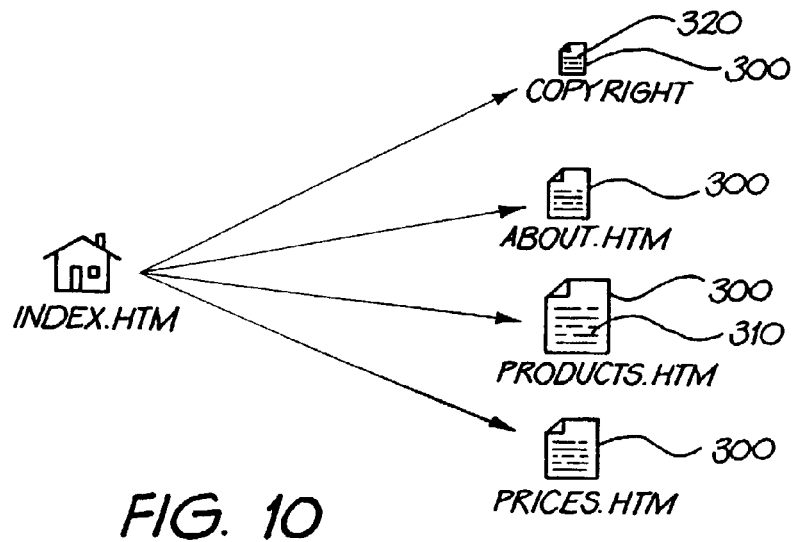
FIG. 10 is an embodiment of a web map which provides information about the sizes of web objects.

A further embodiment of the invention will now be described in which the method shown in FIG. 1 includes a fifth step of providing information about web objects and/or links which correspond to preselected items in a web maps. FIG. 10 shows an application of the fifth step in which information is provided about the size of each object. The size of each object is proportional to the size of an icon 300 representing each corresponding node. FIG. 10 makes it clear that the Products web object 310 is the largest object, while the Copyright object 320 is the smallest.

Figure 11A:
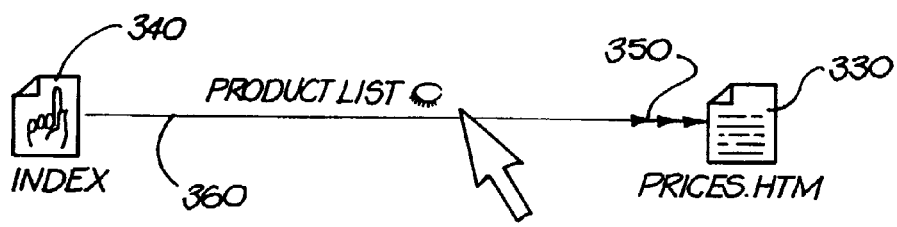
FIG. 11 is an embodiment of a web map which provides information about edges.
Figure 11B:
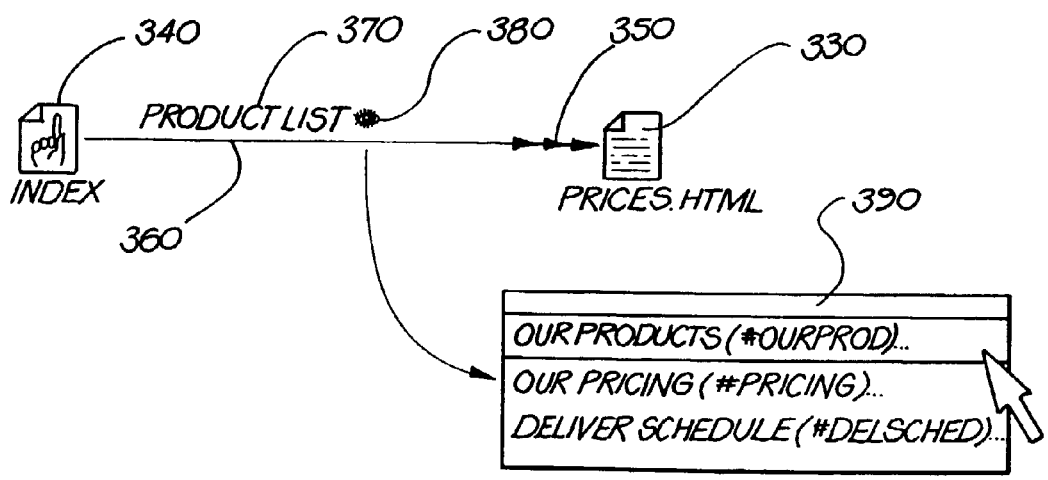

In a further embodiment, information is provided about links, such as the position of a link within an web object, the type of link, the full text of the link, and any attributes or parameters associated with the link in the web object. In FIG. 11(a) the number of links between two objects Prices.html 330 and Index 340 is represented by the number of arrowheads 350 on the corresponding edge 360. In FIG. 11(b) information is provided about each of the links between two web pages 330, 340. The label Product list 370 is the name of the first link from the Index 340 to the Prices 330 pages. When a user clicks on the "eye" icon 380 next to the Product list 370 label, the menu 390 in FIG. 7 appears. This menu shows an itemised list of the links contained in the Index page whose destinations are in the Prices.html page 330. This menu can be used to select one of the links about which more information may then presented.

Figure 12:
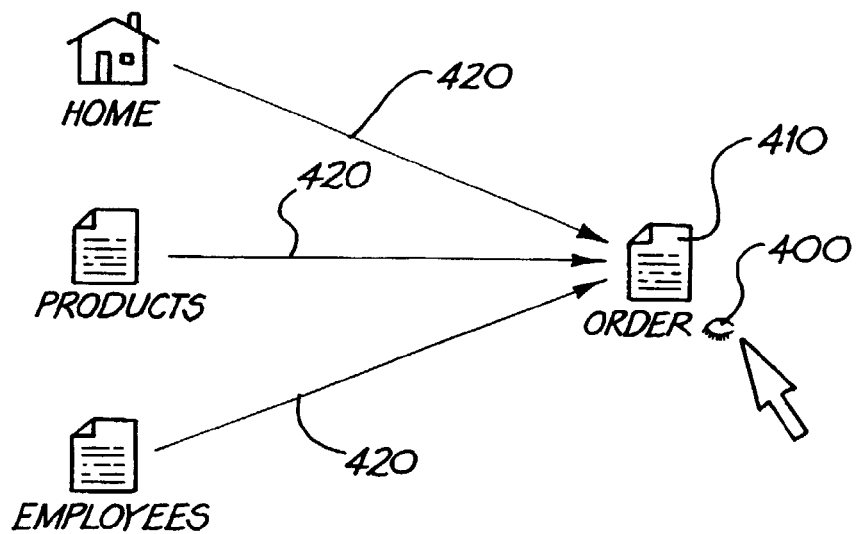
FIG. 12 is a web map which provides information about links to a given web object.

In a further embodiment, information is provided about the links whose destination is a given web object, and about those web objects which are the sources of these links. For example, in FIG. 12 when the user clicks on the eye icon 400 next to the Order node 410, a menu can be invoked showing an itemised list of the links 420 whose destination is the Order page. Such a menu can be used to select one of the links about which more information can then be presented.

Figure 13:
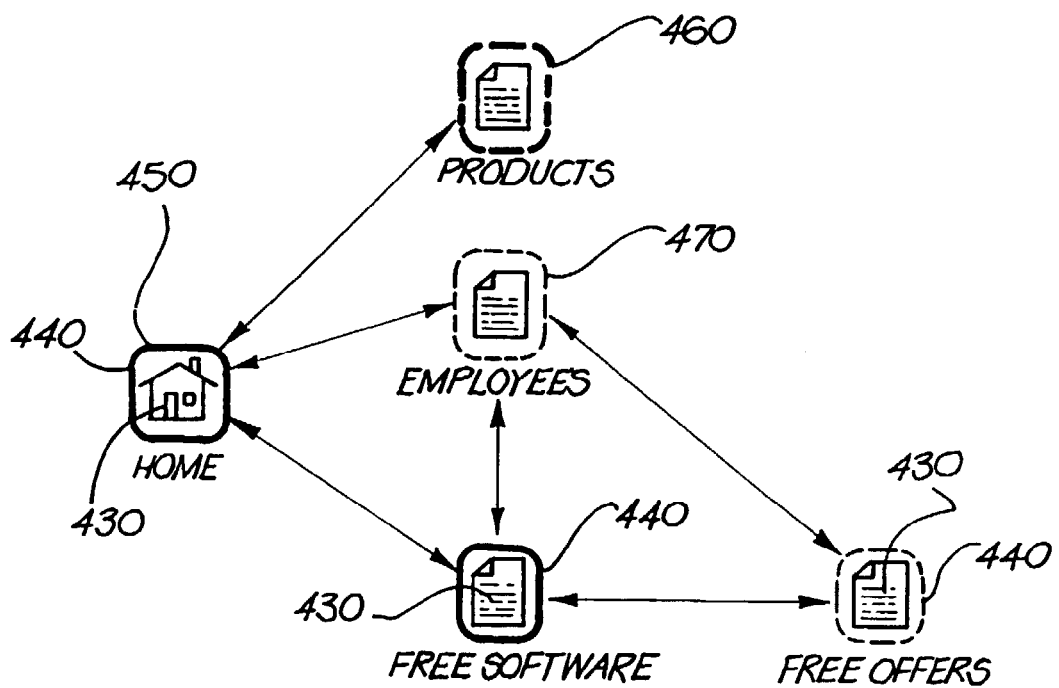
FIG. 13 shows the number of hits to objects by using halos around the objects.

In a further embodiment, information is provided about the dynamic usage ("web traffic") of web objects and links in one or more web sites. Information about the number of times each web object is accessed (its number of "hits") within a given time period is useful for web designers, as it lets them identify popular web objects from which they can guide users to order forms and other priority web objects. It also clearly shows those web objects which are rarely accessed, and may need to be repositioned or discarded. For example, FIG. 13 shows the number of hits in a web site. In this example, the number of hits to each web object is represented by a halo 440 around the corresponding icon 430. A solid halo 450 represents a large number of hits, a thick dashed line 460 represents a medium number of hits, and a thin dashed line 470 represents a low number of hits to a web object within a given time interval. From the web map shown in FIG. 13, it can be clearly seen that the Home page recorded the most hits, followed by Free Software, Products, and then the Employees and Free Offers. In other embodiments, the number of hits is proportional to either the colour, brightness, or line thickness of the halo. It will be understood that many other known methods may be used to graphically indicate the number of hits to each object.

Figure 14:
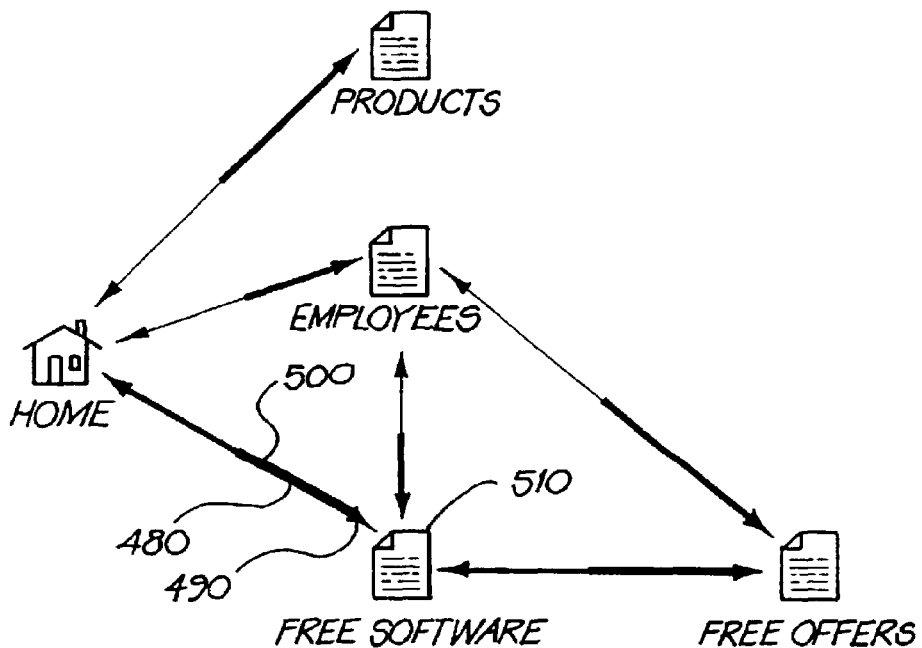
FIG. 14 shows the usage of links in a web site.

In a further embodiment, information is provided about the number of times each link has been followed within a given time period. In addition to showing how often the destination web object of the link has been accessed, this method shows the web designer the paths of links taken by the users when navigating the web site. FIG. 14 shows the usage of the links in a web site. In this example, the thickness of the line 480 and arrowhead 490 making up the half of an edge 500 closest to its destination node 510 is used to represent the usage of the corresponding link. It can clearly be seen that most users navigate from the Home page to the Free Software page, and many then go on to the Free Offers page.

Figure 15:
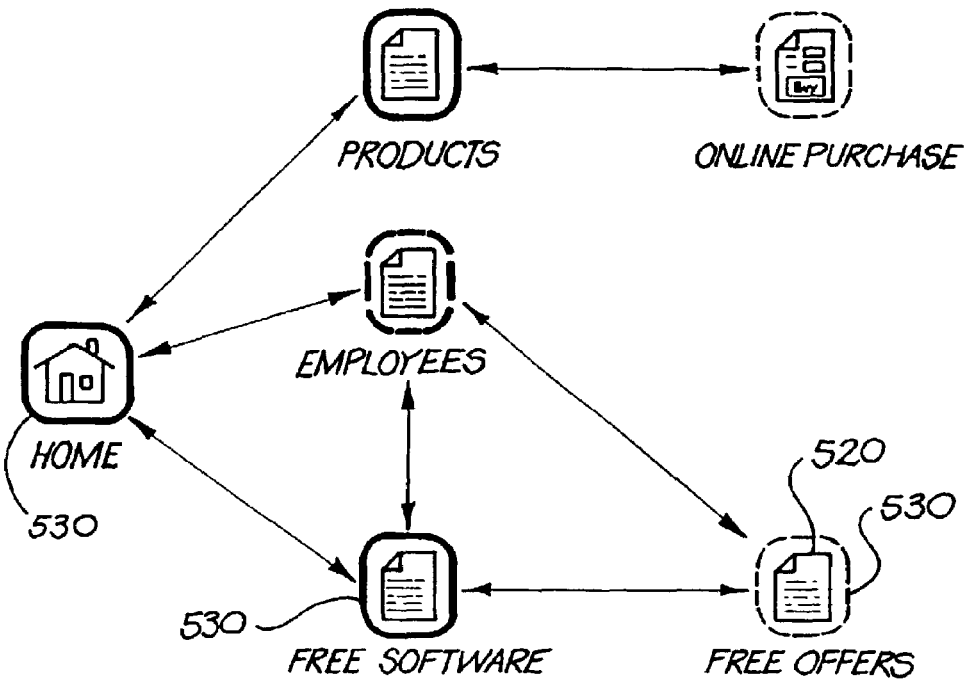
FIG. 15 shows a method of representing the relevance of results of a search query about selected web objects.

In a further embodiment, information is provided in response to a search query from a user. The search query may be about keywords, topics, ideas and other properties or constraints. FIG. 15 shows a method of representing the relevance of each web object 520 with respect to the search query. The relevance of web objects is represented by a halo 530 around the corresponding nodes of the web map. The line thickness and line type in the halo provides a measure of the relevance of each object. This method presents the collection of relevant web objects in a more useful way than methods of the prior art, which typically just list the file names or URLs of the relevant web objects.

Figure 16:
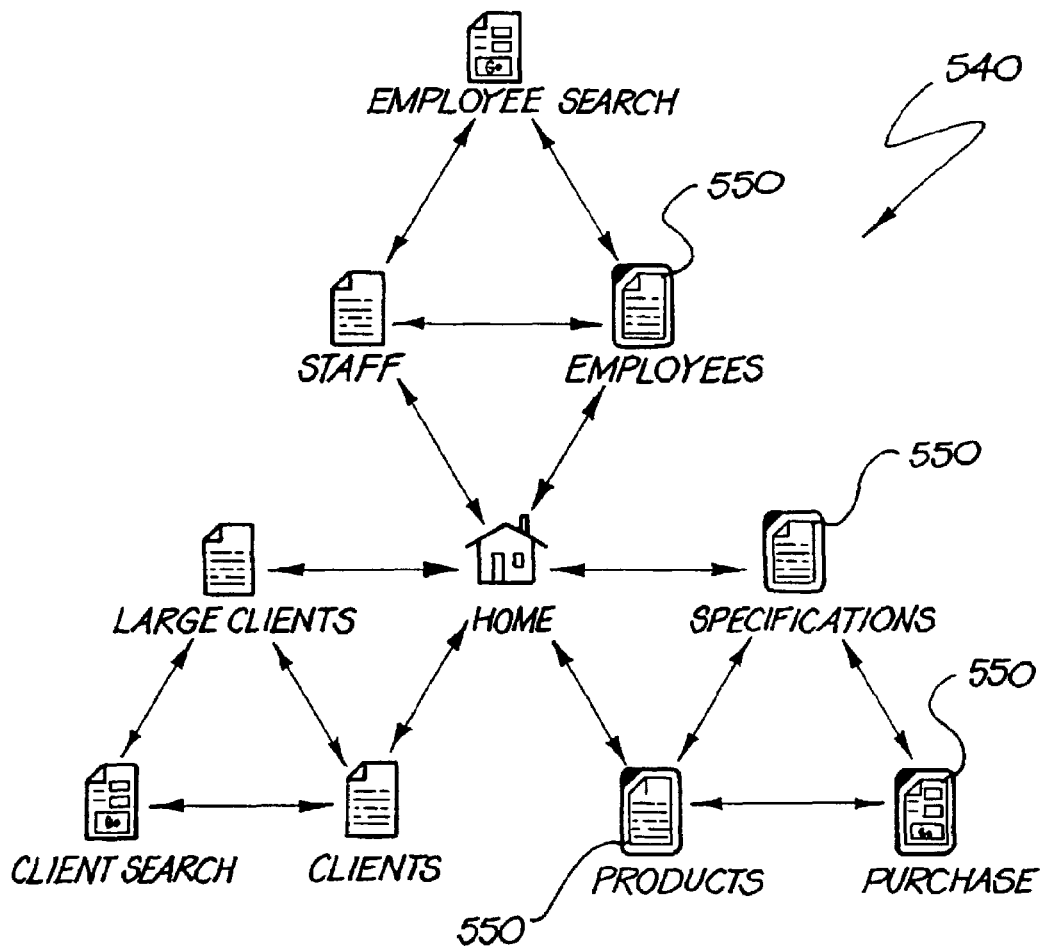
FIG. 16 shows a web map in which four nodes have been selected.
Figure 17:
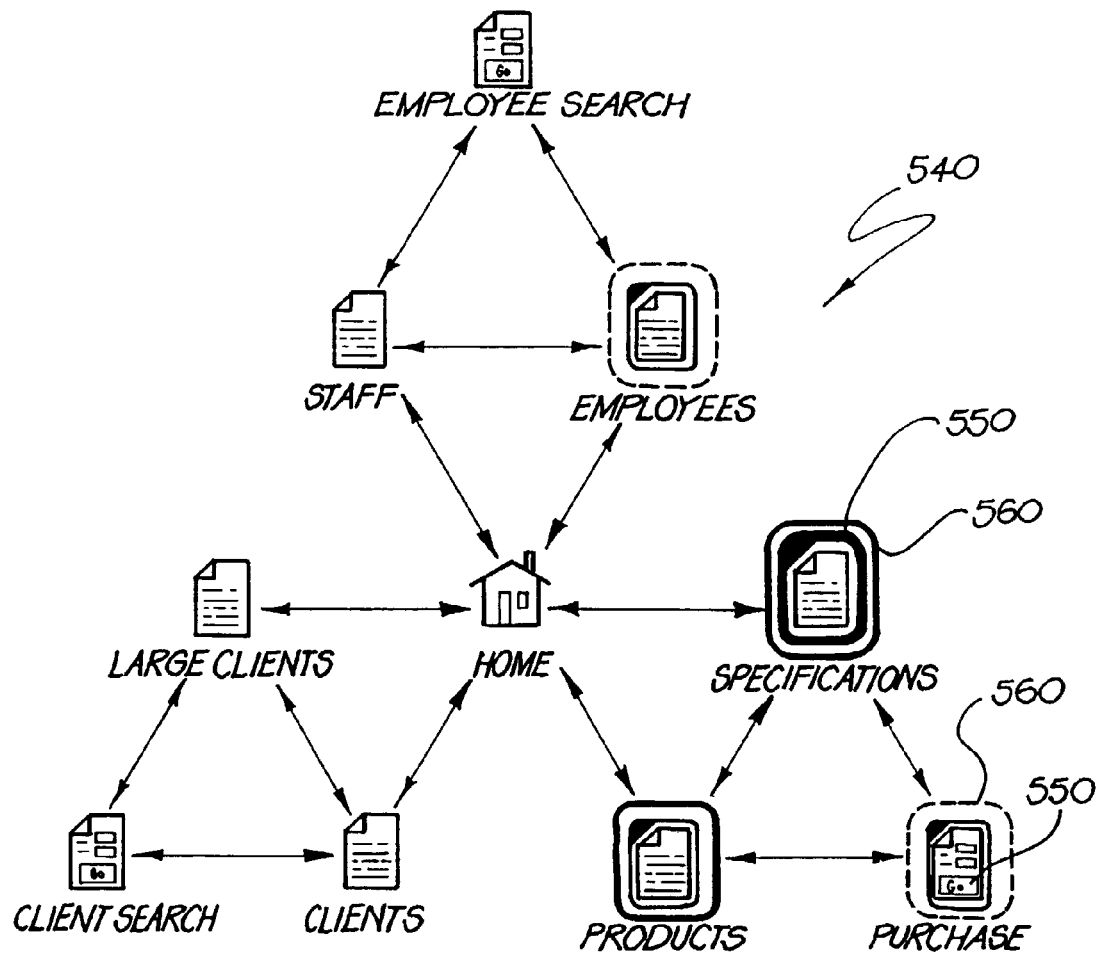
FIG. 17 shows the results of a search limited to the nodes selected in FIG. 16.

In a further embodiment, a subset of the web objects in a web map can be selected by allowing the user to select web objects. A search limited to the selected objects can then be carried out. Limiting the scope of a search in this way can greatly reduce the time taken to perform the search, as well as reducing the number of relevant web objects to be considered by the user after the search is completed. For example, FIG. 16 shows a web map 540 in which four nodes 550 are selected, namely Employees, Specifications, Products and Purchase. FIG. 17 shows the relevance (using halo 560) of selected nodes 550 resulting from the search.

Figure 18:
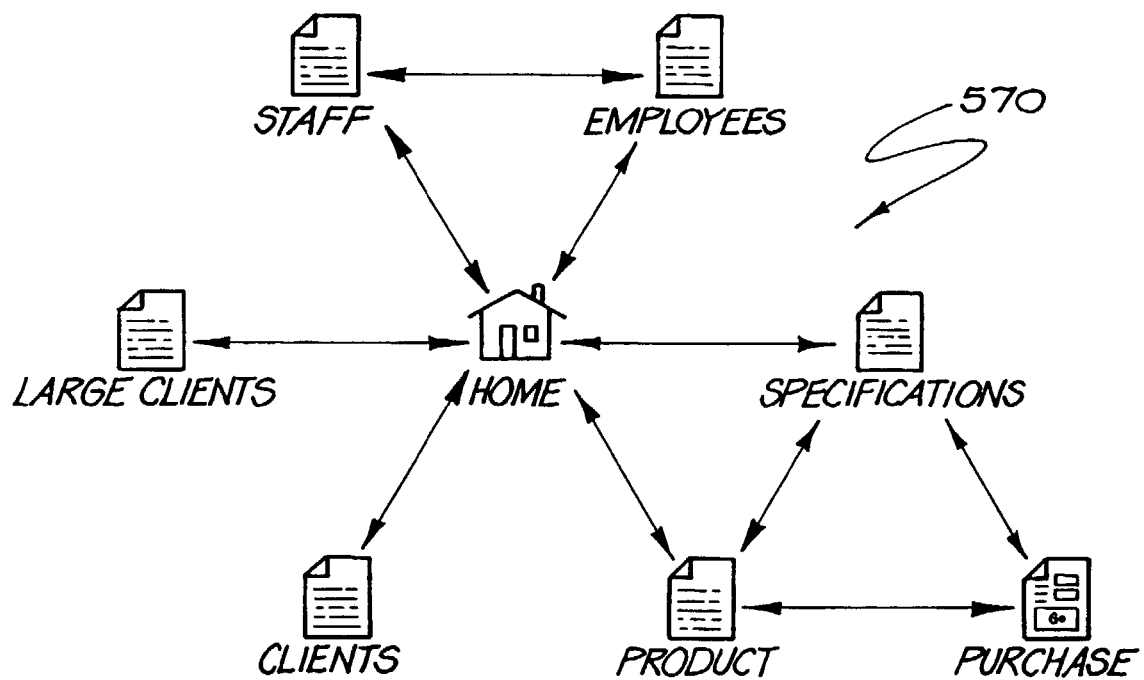
FIG. 18 shows a web map at time A.
Figure 19:
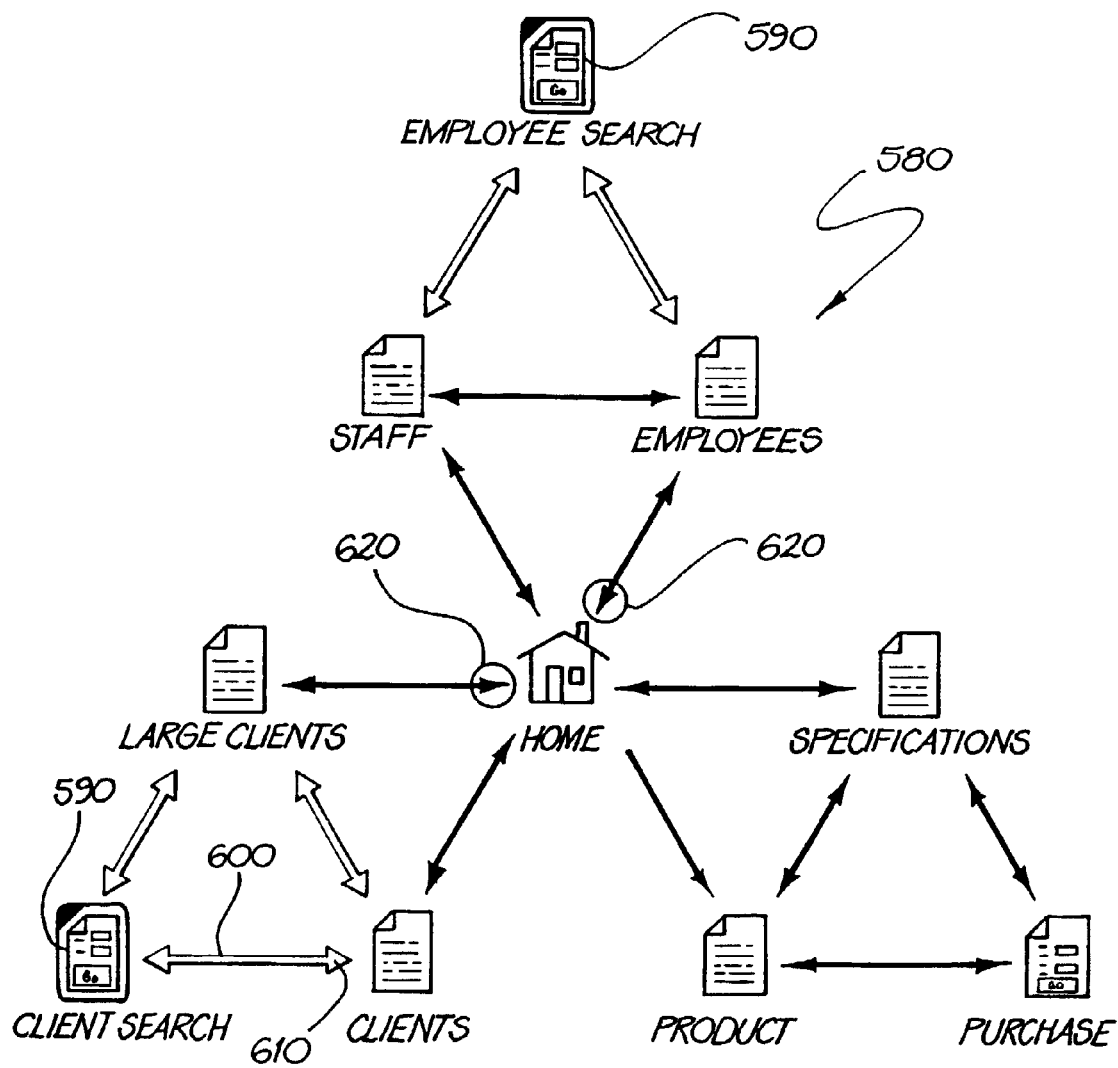
FIG. 19 shows the web map of FIG. 18 at a later time B.

In a further embodiment, information is provided about changes in the structure of a web site over time. For example, FIG. 18 shows a web map 570 of a web site as it existed at time A, and FIG. 19 shows a web map 580 of the same web site as it existed at a later time B. In this example, objects corresponding to the Employee Search and Client Search nodes 590 have been added to the web site these are shown in inverse colours in FIG. 19. New links have also been added to the web site—these are shown as hollow lines 600 with hollow arrowheads 610 in this example. Finally, the links from the Employees and Large Clients web objects to the Home web object have been deleted—these missing links are represented in FIG. 19 with circles 620 around their arrowheads. This method is extremely useful in the maintenance of web sites, and is much more intuitive than the prior art methods, which typically involve a direct comparison with web objects which make up the web site.

A further embodiment of the invention includes a sixth step of modifying a web site in response to a modification of a corresponding web map by a user. One embodiment comprises invoking an external editing program through a web map and using this to modify the represented web sites. In another embodiment, each web map or a section of each web map is associated with a directory in the directory structure of the web sites being represented. By manipulating a node in the web maps, the user can change the directory containing the corresponding web object. This method allows web designers to re-organise the directory structure of a web site without affecting its linking structure. Such re-organisation is often required as a web site grows over time. This is a difficult process using prior art methods, often requiring tedious manual editing of many web objects.

Figure 20:
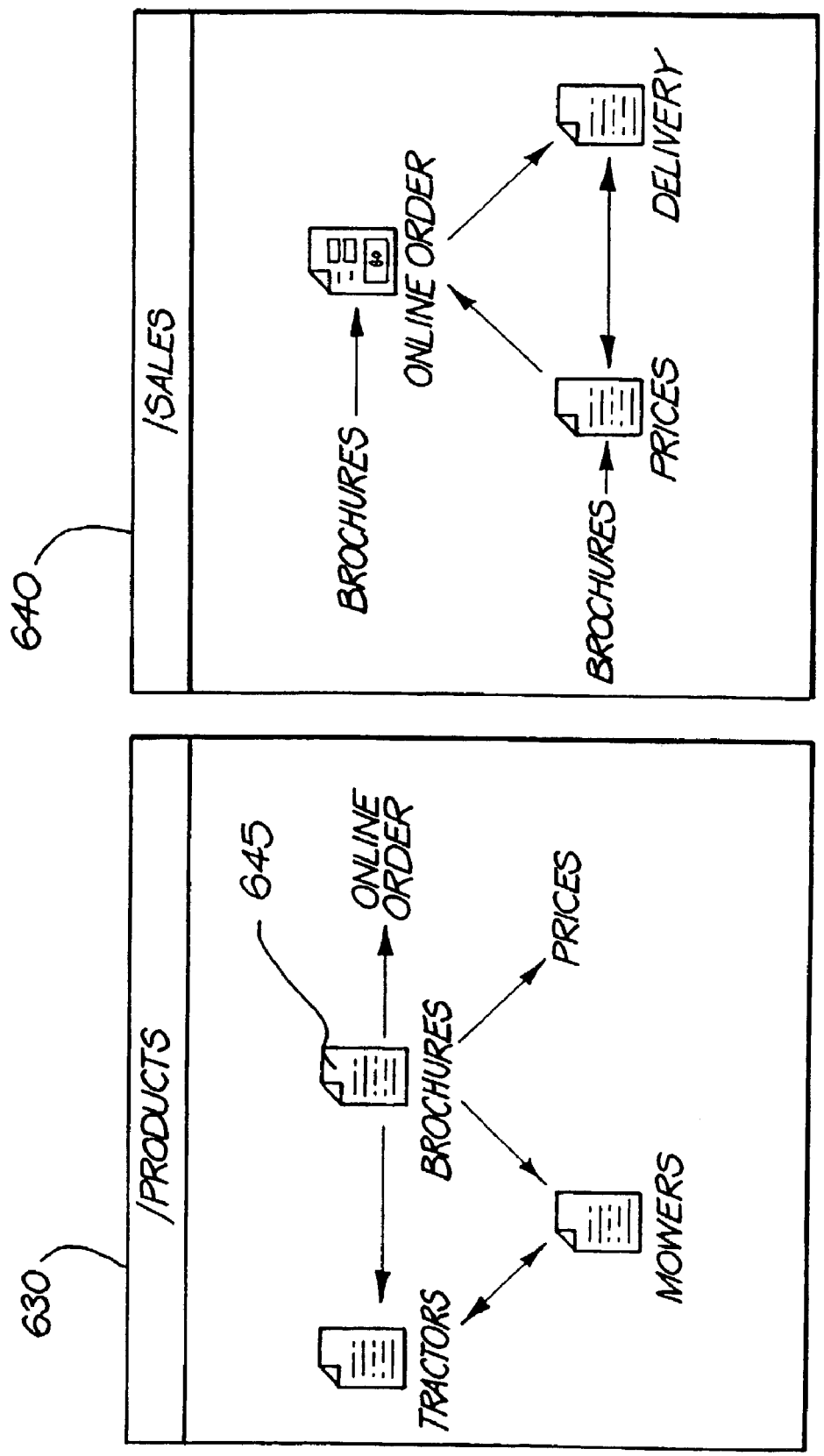
FIG. 20 shows two web maps before being modified.
Figure 21:
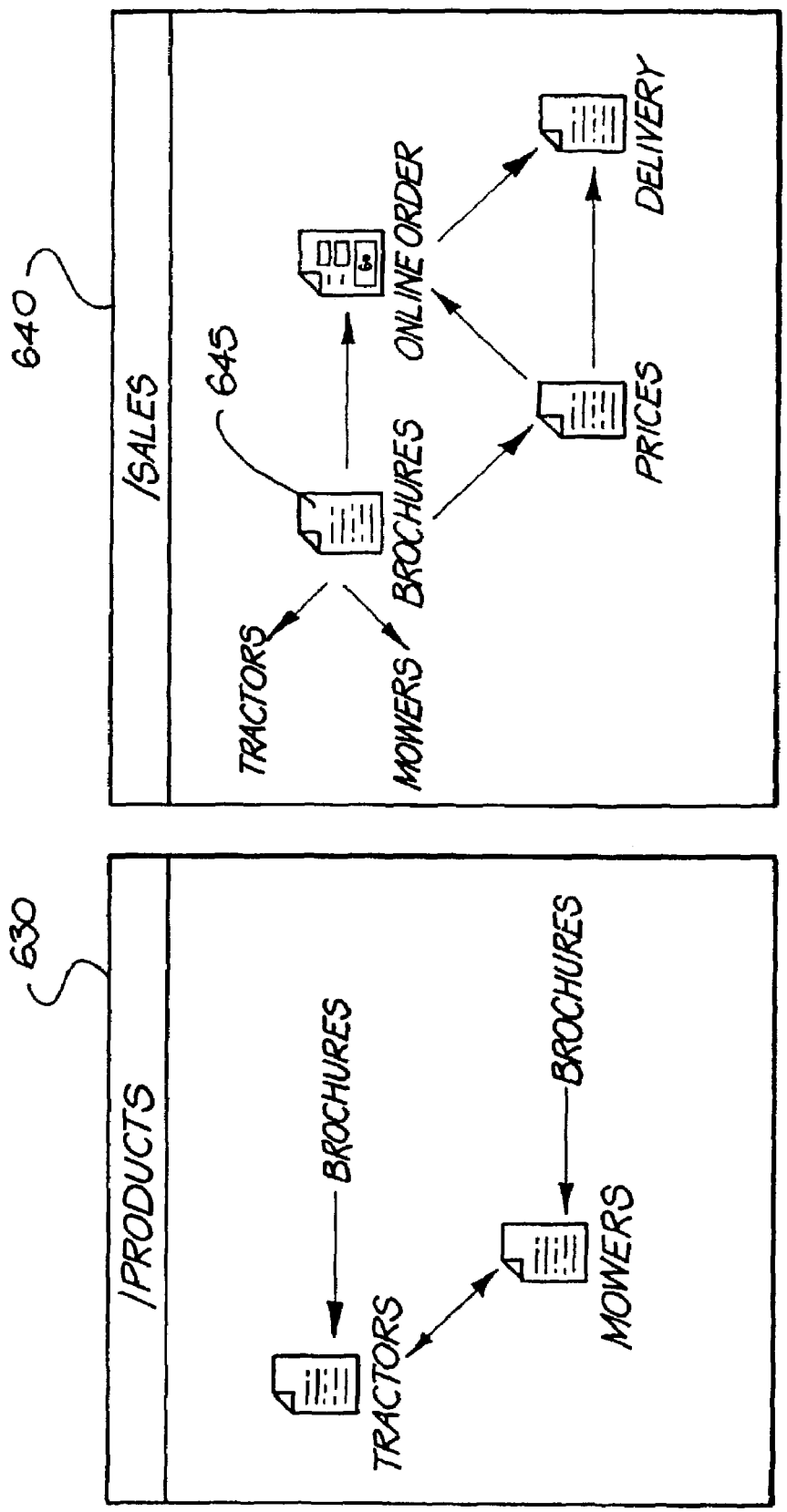
FIG. 21 shows the web maps of FIG. 20 after being modified.

For example, FIG. 20 shows two web maps 630, 640 the web map 630 on the left represents the Products directory of a web site, while the web map 640 on the right represents the Sales directory of the same web site. If the web designer decides to move the Brochures web object into the Sales directory, the node 645 corresponding to the Brochures web object may simply be moved into the web map representing the Products directory. FIG. 21 shows the result of this move.

Figure 22:
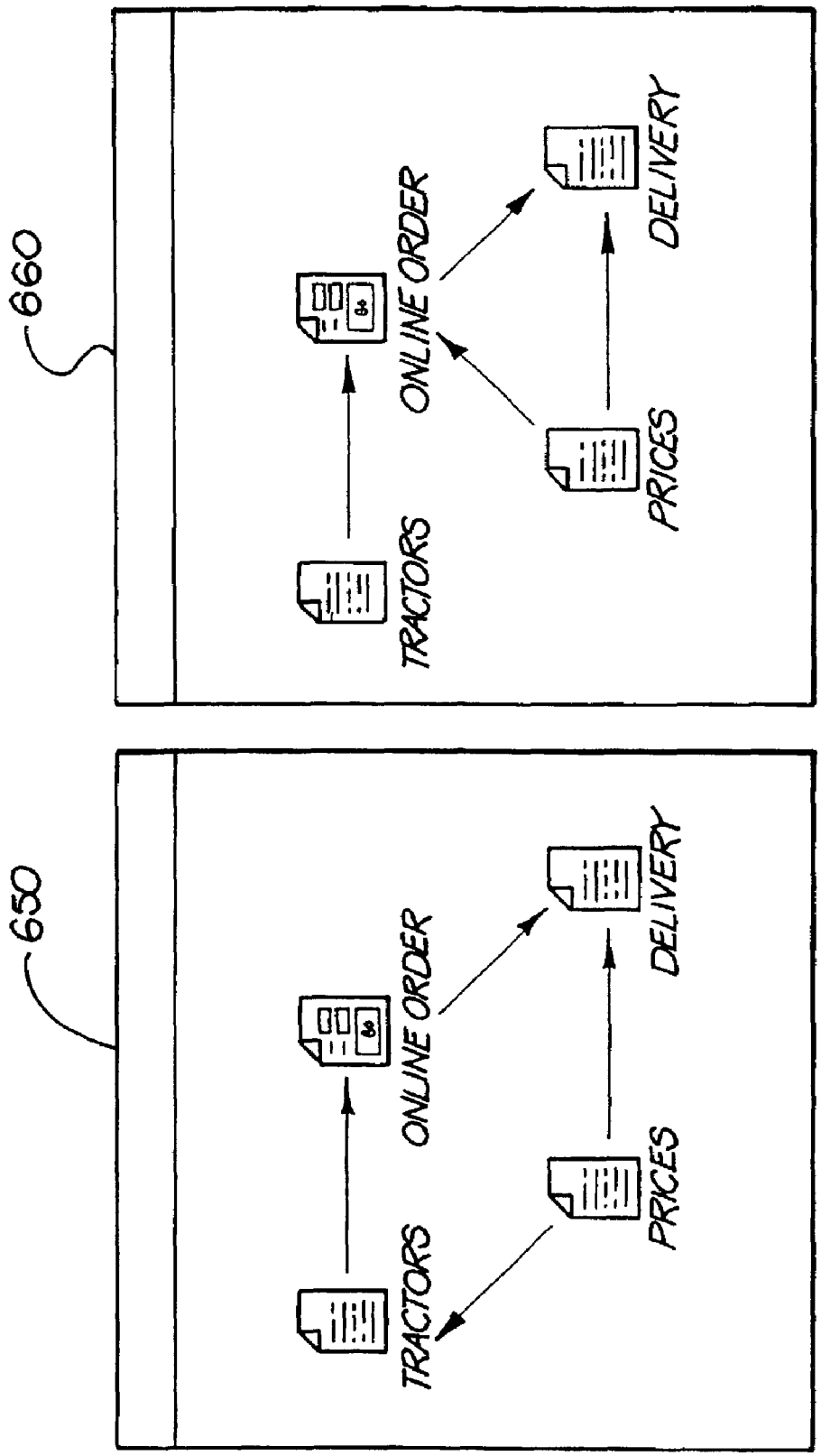
FIG. 22 shows a web map before and after being modified.

In another example, the method is used to change the destination of a link. For example, the left side of FIG. 22 shows a web map 650 representing a web site. To change the link between the Prices web object and the Tractors web object into a link between the Prices web object and the Online Order web object, the web designer simply needs to select the corresponding edge and then select its new destination node. The resulting web map 660 is shown in the right side of FIG. 22.

Figure 23:
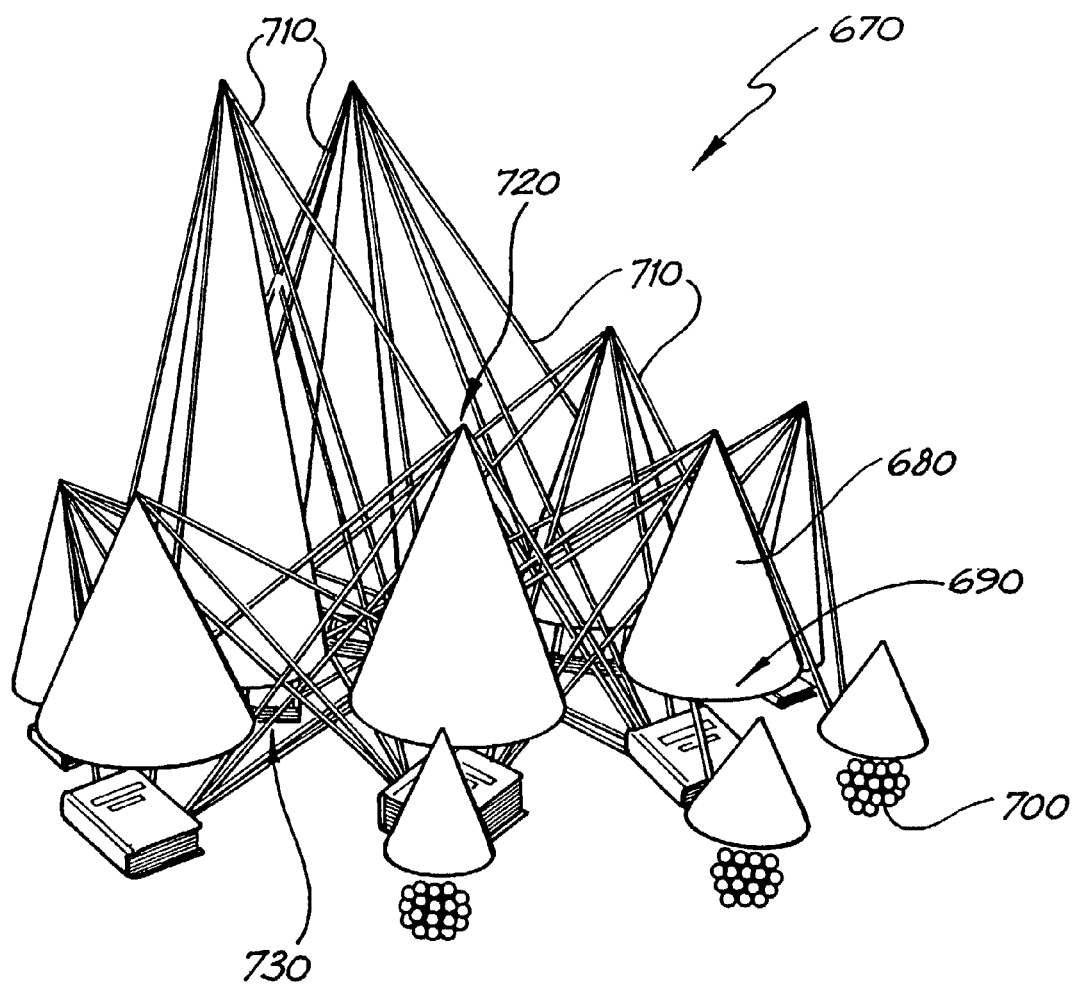
FIG. 23 shows a three dimensional representation of a web map.

Information about a web site can be presented in a three-dimensional web map. FIG. 23 shows an example of a three-dimensional web map 670 of a web site. In this example, each web object is represented by a cone 680, where the width of the base 690 of each cone is proportional to the number of links whose destination is the corresponding web object, and the height of each cone is proportional to the number of links whose source is the corresponding web object. The base 690 of each cone is also labelled with an icon 700 representing the type of the corresponding web object, and either its title or its URL. Each link is represented by a pipe 710 running from the top 720 of its source cone to the base of its destination cone 730, giving the visual impression that the link flows down from its source to its destination.

Figure 24:
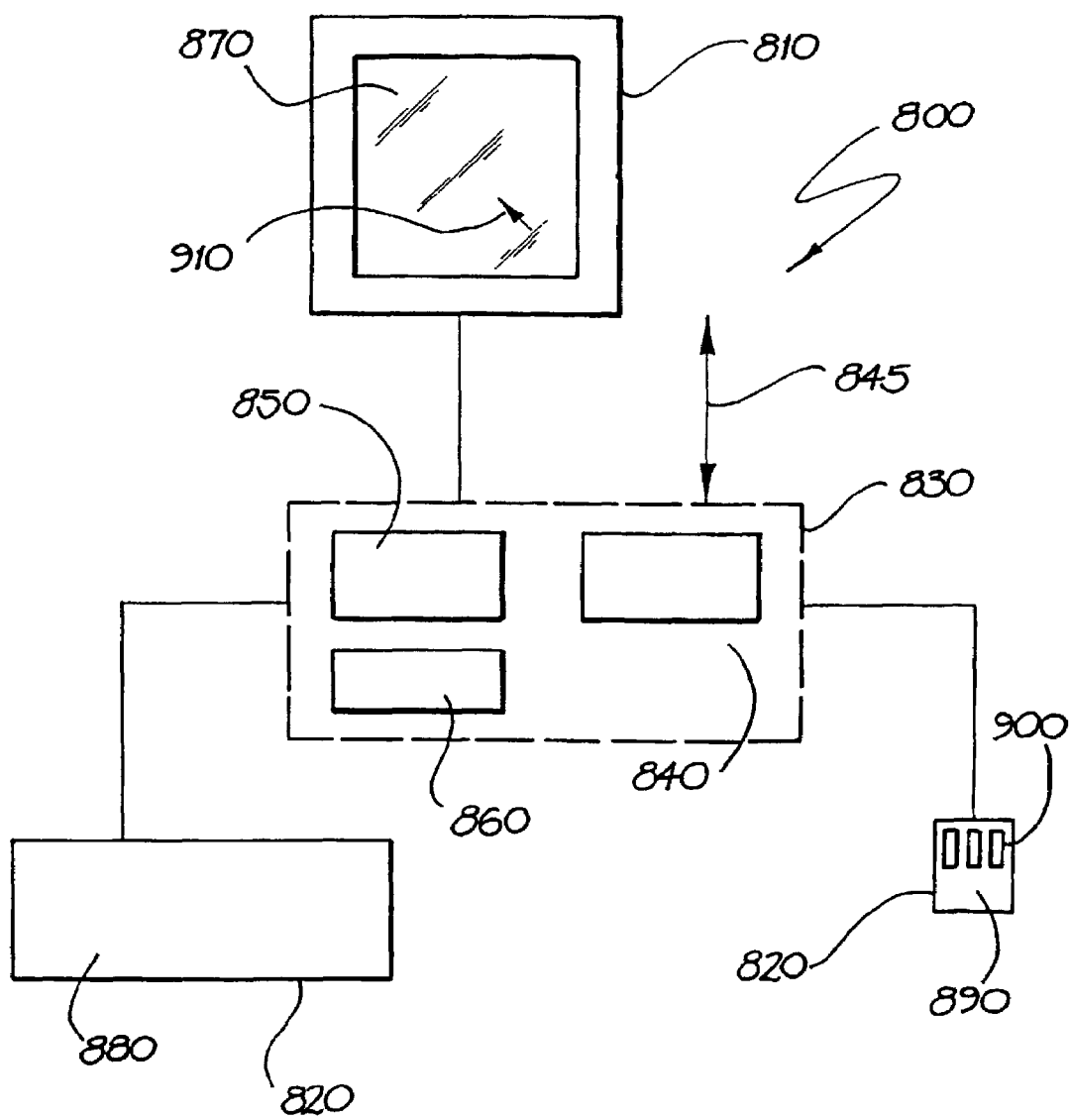
FIG. 24 shows a schematic of a computer system suitable for implementing at least some embodiments of the invention.

All of the methods of the present invention can be implemented with a system which comprises hardware, such as a PC, and appropriate software. In one embodiment, shown in FIG. 24, the hardware 800 comprises a graphics display device 810, input devices 820, and a system chassis 830 which includes memory 840, a processor 850, and a medium 860 such as a disk drive for storing files. The processor 850 generates a display on a screen 870 of the display device 810 by executing a program stored in the memory 840. The program uses data which is also stored in the memory 840. At least some of the data for a web map may be obtained from a non-local web site via a network connection 845. If the program is interactive, execution of the program is controlled by inputs from interactive input devices 820 which in this example comprise a keyboard 880 and mouse 890 with three buttons 900. A pointer 910 on the screen 870 follows the movement of the mouse. The pointer 910 can be used to manually select nodes or edges in a web map.

It would be appreciated by a person skilled in the art that numerous variations and/or modifications may be made to the present invention as shown in the specific embodiments without departing from the spirit or scope of the invention as broadly described. The present embodiments are therefore to be considered in all respects to be illustrative and not restrictive.

The claims defining the invention are as follows:

1. A method of mapping at least a part of one or more web sites having web objects and web links, whereby web objects and links are mapped as nodes and edges, respectively, in one or more web maps, each object being mapped to at least one corresponding node, and there being only one corresponding object for each node, the method comprising the steps of:
   (a) selecting one or more sets of items for display in the respective one or more web maps, wherein items include nodes and edges corresponding to the web objects and links in at least one web map;
   (b) displaying the one or more sets of items in the respective one or more web maps;
   (c) selecting at least one item from the displayed sets of items; and
   (d) re-displaying the at least one item in at least one web map such that the item is distinguished from any other item in the web map, wherein step (a) comprises the following sub-step:
   (a1) for each of the objects in the part(s) of the web site(s) to be mapped, adding nodes to the sets of the items such that similar nodes are added to the same set, wherein the similarity of each node and an associated similar node is determined by:
   determining a directory distance, being a measure of the length of a shortest path between a pair of web objects corresponding to the node and the associated similar node in a directory structure of the one or more web sites, wherein the directory structure comprises a physical arrangement of web objects on one or more machines hosting the web site(s);
   determining a link distance, being a measure of the length of the shortest path between a pair of web objects corresponding to the node and the associated similar node in a linking structure of the one or more web sites;
   applying weights to the determined directory and link distances and combining the weighted directory and link distances; and
   determining the similarity based on the combined weighted directory and link distances.

2. The method of claim 1, wherein step (d) comprises re-displaying the web map in a clarified form.

3. The method of claim 2, wherein re-displaying the web map in a clarified form comprises a step of de-cluttering the web map.

4. The method of claim 3, wherein step (a) further comprises the following sub-step:
   (a2) for each object which corresponds to a node added to the set, adding a new node to the set for any other object which is either the source of a link to the object, or a destination of a link from the object.

5. The method of claim 4, wherein step (a) further comprises the following sub-step:
   (a3) for each pair of nodes in each web map, adding an edge between the pair of nodes if there is a link between a pair of objects corresponding to the nodes.

6. The method of claim 1, wherein steps (b) and (d) comprise re-displaying items in a graphical format.

7. The method of claim 1, wherein step (d) comprises re-displaying the at least one item selected in step (c) while not re-displaying any other items in the web map.

8. The method of claim 1, wherein step (c) comprises a sub-step of automatically selecting at least one item.

9. The method of claim 1, wherein step (c) comprises a sub-step of selecting at least one item by searching through items in at least one web map with a searching tool, and selecting at least one of the searched items based on at least one predetermined selection criterion.

10. The method of claim 1, wherein step (c) comprises a sub-step of manually selecting at least one item.

11. The method of claim 1, wherein step (c) comprises selecting the at least one item by one or more of the following techniques:
   manual selection by a user, wherein selection of the item(s) is carried out by a user using a searching tool with at least one predetermined selection criterion; or
   automatic selection, wherein the type(s) of selection technique(s) used is chosen by a user and selection of the item(s) is carried out automatically.

12. The method of claim 9, wherein each predetermined selection criterion is determined by a user.

13. The method of claim 9, wherein each predetermined selection criterion comprises selecting an item if the item possesses one or more specified properties and/or attributes.

14. The method of claim 13, wherein the one or more specified properties and/or attributes are chosen from the following:
   the type of each web object which corresponds to a node to be searched;
   the form of each web object which corresponds to a node to be searched;
   traffic-derived properties of each web object which corresponds to a node to be searched;
   a set of keywords, ideas, topics, or data patterns to be found within each web object which corresponds to a node to be searched;
   the size of each web object which corresponds to a node to be searched;
   whether each web object which corresponds to a node to be searched is part of the web sites being mapped by the web map, or a web object on another web site;
   whether each web object which corresponds to a node to be searched is a web page containing frames; and
   whether each web object which corresponds to a node to be searched is a web page containing forms.

15. The method of claim 1, further comprising the step of:
   providing information about one or more web objects and/or links which correspond to one or more preselected items in the one or more web maps.

16. The method of claim 15, wherein the one or more preselected items is the item or items selected in step (c).

17. The method of claim 15, wherein the step of providing information comprises a sub-step of preselecting one or more items from the one or more web maps.

18. The method of claim 17, wherein the preselected item(s) are chosen by a user.

19. The method of claim 17, wherein the sub-step of preselecting one or more items comprises selecting the item(s) by one or more of the following techniques:
   manual selection by a user, wherein selection by a user of the item(s) is carried out using a searching tool with at least one predetermined selection criterion; or
   automatic selection, wherein the type(s) of selection technique(s) used is chosen by a user and the selection of item(s) is carried out automatically.

20. The method of claim 15, wherein the information provided about web objects and/or links comprises information about one or more of the following:
   the type of each web object which corresponds to a preselected node;
   the form of each web object which corresponds to a preselected node;
   traffic-derived properties of each web object which corresponds to a preselected node;
   a set of keywords, ideas, topics, or data patterns to be found within each web object which corresponds to a preselected node;
   the size of each web object which corresponds to a preselected node;
   whether each web object which corresponds to a preselected node is part of the web sites being mapped by the web map, or a web object on another web site;
   whether each web object which corresponds to a preselected node is a web page containing frames;
   whether each web object which corresponds to a preselected node is a web page containing forms; and
   any changes over a predetermined time interval which have been made to each web object corresponding to a preselected node.

21. The method of claim 1, further comprising the step of:
   modifying the one or more web sites in response to a modification of a corresponding web map by a user.

22. The method of claim 21, further comprising the step of:
   re-displaying at least one web map after the web map has been modified.

23. A method of providing information to a third party computer program about at least a part of one or more web sites having web objects and web links, the method comprising the steps of:
   mapping the web objects and links as virtual nodes and virtual edges, respectively, in one or more virtual web maps, each object being mapped to at least one corresponding virtual node, and there being only one corresponding object for each virtual node;
   selecting one or more sets of items from the one or more virtual web maps, wherein items include virtual nodes and virtual edges corresponding to the web objects and links in at least one web map;
   providing information about the selected one or more sets of items to an application programming interface suitable for transmitting at least some of the information to a third party computer program;
   wherein the step of selecting comprises the following sub-step:
   for each of the mapped objects of the web sites, adding nodes to the sets of items such that similar nodes are added to the same set, wherein the similarity of each node and an associated similar node is determined by:
   determining a directory distance, being a measure of the length of a shortest path between a pair of web objects corresponding to the node and the associated similar node in a directory structure of the one or more web sites, wherein the directory structure comprises a physical arrangement of web objects on one or more machines hosting the web site(s);
   determining a link distance, being a measure of the length of the shortest path between a pair of web objects corresponding to the node and the associated similar node in a linking structure of the one or more sites;
   applying weights to the determined directory and link distances and combining the weighted directory and link distances; and
   determining the similarity based on the combined weighted directory and link distances.

24. The method of claim 23, wherein the third party program comprises spreadsheet software.

25. The method of claim 23, wherein the third party program comprises graphics software.

26. The method of claim 23 wherein the step of selecting further comprises the following sub-step:
   for each object which corresponds to a node added to the set, adding a new node to the set for any other object which is either the source of a link to the object, or a destination of a link from the object.

27. The method of claim 26, wherein the step of selecting further comprises the following sub-step:
   for each pair of nodes in each web map, adding an edge between the pair of nodes if there is a link between a pair of objects corresponding to the nodes.

28. A computer readable medium storing instructions for performing a method for controlling a computing device to map at least a part of one or more web sites having web objects and web links, whereby web objects and links are mapped as nodes and edges, respectively, in one or more web maps, each object being mapped to at least one corresponding node, and there being only one corresponding object for each node, the method comprising the steps of:
   (a) selecting one or more sets of items for display in the respective one or more web maps, wherein items include nodes and edges corresponding to the web objects and links in at least one web map;
   (b) displaying the one or more sets of items in the respective one or more web maps;
   (c) selecting at least one item from the displayed sets of items; and
   (d) re-displaying the at least one item in at least one web map such that the item is distinguished from any other item in the web map, wherein step (a) comprises the following sub-step:
      (a1) for each of the objects in the part(s) of the web site(s) to be mapped, adding nodes to the sets of the items such that similar nodes are added to the same set, wherein the similarity of each node and an associated similar node is determined by:
      determining a directory distance, being a measure of the length of a shortest path between a pair of web objects corresponding to the node and the associated similar node in a directory structure of the one or more web sites, wherein the directory structure comprises a physical arrangement of web objects on one or more machines hosting the web site(s);
      determining a link distance, being a measure of the length of the shortest path between a pair of web objects corresponding to the node and the associated similar node in a linking structure of the one or more web sites;

applying weights to the determined directory and link distances and combining the weighted directory and link distances; and determining the similarity based on the combined weighted directory and link distances.

29. A system for mapping at least a part of one or more web sites having web objects and web links, whereby web objects and links are mapped as nodes and edges, respectively, in one or more web maps, each object being mapped to at least one corresponding node, and there being only one corresponding object for each node, the system comprising:

means for selecting one or more sets of items for display in the respective one or more web maps, wherein items include nodes and edges corresponding to the web objects and links in at least one web map;

means for displaying the one or more sets of items in the respective one or more web maps;

means for selecting at least one item from the displayed sets of items; and means for re-displaying the at least one item in at least one web map such that the item is distinguished from any other item in the web map, wherein said means for selecting said one or more sets of items, for each of the objects in the part(s) of the web site(s) to be mapped, adds nodes to the sets of the items such that similar nodes are added to the same set, and includes means for determining the similarity of each node and an associated similar node by:

determining a directory distance, being a measure of the length of a shortest path between a pair of web objects corresponding to the node and the associated similar node in a directory structure of the one or more web sites, wherein the directory structure comprises a physical arrangement of web objects on one or more machines hosting the web site(s);

determining a link distance, being a measure of the length of the shortest path between a pair of web objects corresponding to the node and the associated similar node in a linking structure of the one or more web sites;

applying weights to the determined directory and link distances and combining the weighted directory and link distances; and determining the similarity based on the combined weighted directory and link distances.

30. A system for providing information to a third party computer program about at least a part of one or more web sites having web objects and web links, the system comprising:

means for mapping the web objects and links as virtual nodes and virtual edges, respectively, in one or more virtual web maps, each object being mapped to at least one corresponding virtual node, and there being only one corresponding object for each virtual node;

means for selecting one or more sets of items from the one or more virtual web maps, wherein items include virtual nodes and virtual edges corresponding to the web objects and links in at least one web map;

means for providing information about the selected one or more sets of items to an application programming interface suitable for transmitting at least some of the information to a third party computer program, wherein said means for selecting said one or more sets of items, for each of the mapped objects of the web sites, adds nodes to the sets of items such that similar nodes are added to the same set, and includes means for determining the similarity of each node and an associated similar node by;

determining a directory distance, being a measure of the length of a shortest path between a pair of web objects corresponding to the node and the associated similar node in a directory structure of the one or more web sites, wherein the directory structure comprises a physical arrangement of web objects on one or more machines hosting the web site(s);

determining a link distance, being a measure of the length of the shortest path between a pair of web objects corresponding to the node and the associated similar node in a linking structure of the one or more sites;

applying weights to the determined directory and link distances and combining the weighted directory and link distances; and determining the similarity based on the combined weighted directory and link distances.

31. The method of claim 11, wherein each predetermined selection criterion is determined by a user.

32. The method of claim 1, wherein the sets of items are displayed in a plurality of web maps, and each web map in the plurality of web maps is different and distinct from the other web maps.

33. The method of claim 23, wherein the sets of items are displayed in a plurality of virtual web maps, and each virtual web map in the plurality of virtual web maps is different and distinct from the other virtual web maps.

34. A method of mapping at least a part of one or more web sites having web objects and web links, whereby web objects and links are mapped as nodes and edges, respectively, in a plurality of web maps, each object being mapped to at least one corresponding node, and there being only one corresponding object for each node, the method comprising the steps of:

(a) selecting sets of items for display in the plurality of web maps, wherein items include nodes and edges corresponding to the web objects and links in the web maps;

(b) displaying the plurality of web maps with one or more sets of items in a respective web map such that each web map in the plurality of web maps is different and distinct from the other web maps;

(c) selecting at least one item from the displayed sets of items; and (d) re-displaying the at least one item in at least one web map such that the item is distinguished from any other item in the web map, wherein step (a) comprises the following sub-step:

(a1) for each of the objects in the part(s) of the web site(s) to be mapped, adding nodes to the sets of the items such that similar nodes are added to the same set, wherein the similarity of each node and an associated similar node is determined by:

determining a directory distance, being a measure of the length of a shortest path between a pair of web objects corresponding to the node and the associated similar node in a directory structure of the one or more web sites, wherein the directory structure comprises a physical arrangement of web objects on one or more machines hosting the web site(s);

determining a link distance, being a measure of the length of the shortest path between a pair of web objects corresponding to the node and the associated similar node in a linking structure of the one or more web sites;

applying weights to the determined directory and link distances and combining the weighted directory and link distances; and determining the similarity based on the combined weighted directory and link distances.

* * * * *